(12) United States Patent
Saxell et al.

(10) Patent No.: US 8,101,780 B2
(45) Date of Patent: Jan. 24, 2012

(54) CRYSTALLINE FORM OF 3-(DIFLUORMETHYL)-1-METHYL-N-(3',4',5'-TRIFLUOR[1,1'-BIPHENYL]-2-YL)-1H-PYRAZOL-4-CARBOXAMIDE

(75) Inventors: Heidi Emilia Saxell, Carlsberg (DE); Jochen Dietz, Mannheim (DE); Sebastian Peer Smidt, Mannheim (DE); Cedric Dieleman, Scheibenhard (FR)

(73) Assignee: BASF SE, Ludwigshafen (DE)

( * ) Notice: Subject to any disclaimer, the term of this patent is extended or adjusted under 35 U.S.C. 154(b) by 195 days.

(21) Appl. No.: 12/668,242

(22) PCT Filed: Jul. 7, 2008

(86) PCT No.: PCT/EP2008/058785
§ 371 (c)(1),
(2), (4) Date: Jan. 8, 2010

(87) PCT Pub. No.: WO2009/007344
PCT Pub. Date: Jan. 15, 2009

(65) Prior Publication Data
US 2010/0255996 A1    Oct. 7, 2010

(30) Foreign Application Priority Data
Jul. 12, 2007 (EP) .................................. 07112393

(51) Int. Cl.
*C07D 231/10* (2006.01)

(52) U.S. Cl. .................................................. 548/374.1
(58) Field of Classification Search ................ 548/374.1
See application file for complete search history.

(56) References Cited

U.S. PATENT DOCUMENTS
2008/0293798 A1    11/2008 Dietz et al.

FOREIGN PATENT DOCUMENTS
WO    WO 2006/087343    8/2006
WO    WO 2007/017416    2/2007

OTHER PUBLICATIONS

International Search Report completed Nov. 21, 2008, in International Application No. PCT/EP2008/058785, filed Jul. 7, 2008.
International Preliminary Report on Patentability dated Jan. 21, 2010, from corresponding International Application No. PCT/EP2008/058785, filed Jul. 7, 2008.

*Primary Examiner* — Rebecca Anderson
*Assistant Examiner* — Samantha Shterengarts
(74) *Attorney, Agent, or Firm* — Brinks Hofer Gilson & Lione

(57) ABSTRACT

The present invention relates to a new crystalline form of 3-(Difluormethyl)-1-methyl-N-(3',4',5'-trifluor[1,1'-biphenyl]-2-yl)-1H-pyrazol-4-carboxamide. The invention also relates to processes for the production of this crystalline form and formulations for plant protection which contain the crystalline form of 3-(Difluormethyl)-1-methyl-N-(3',4',5'-trifluor[1,1'-biphenyl]-2-yl)-1H-pyrazol-4-carboxamide.

16 Claims, 15 Drawing Sheets

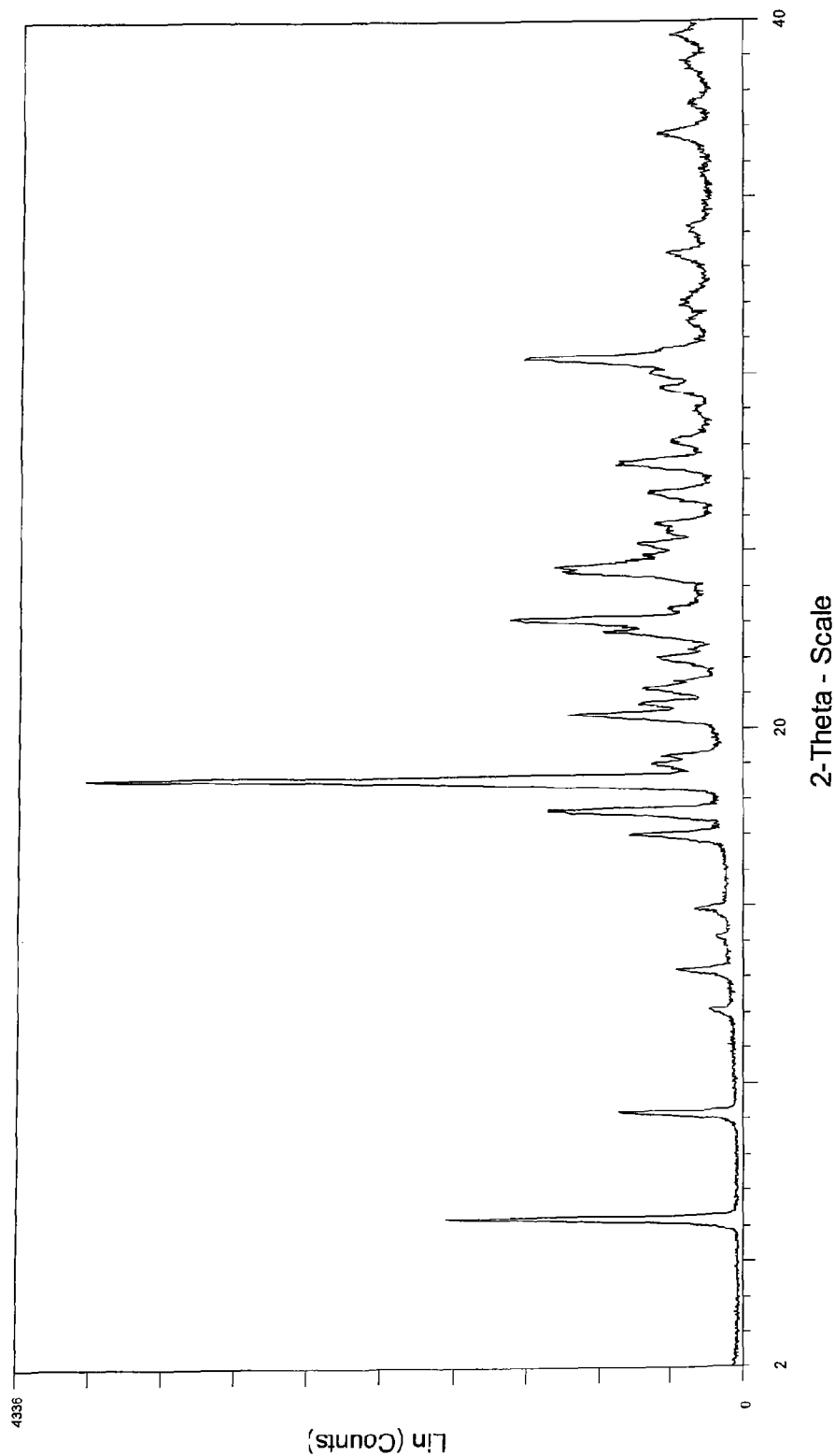
FIGURE 1. Powder X-ray diffractogram of form B.

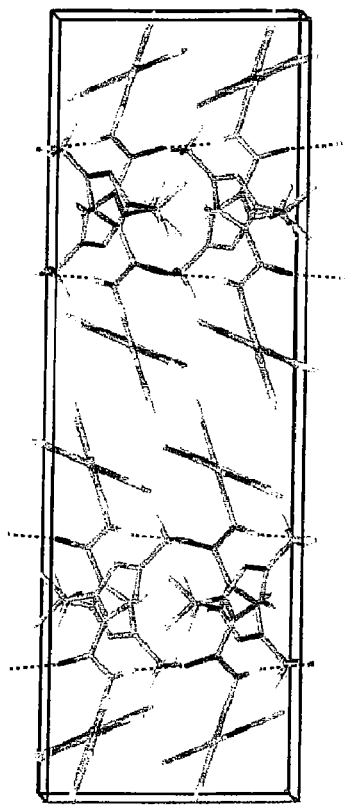
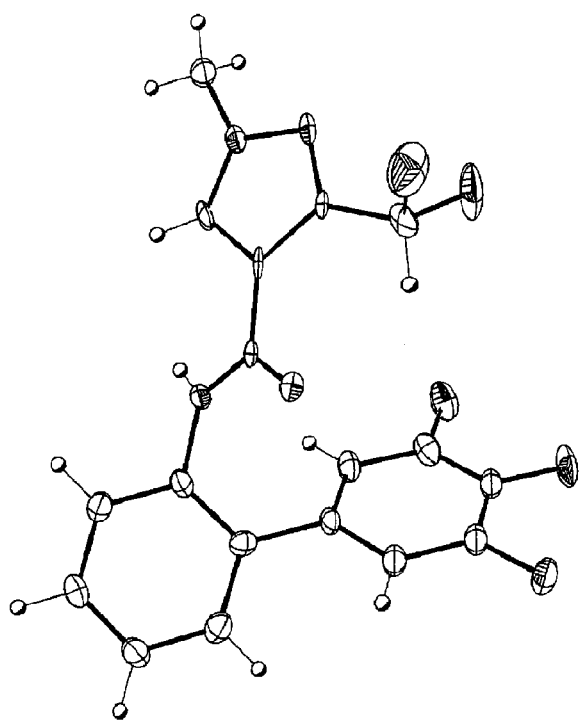
FIGURE 2. Single crystal structure of form B.

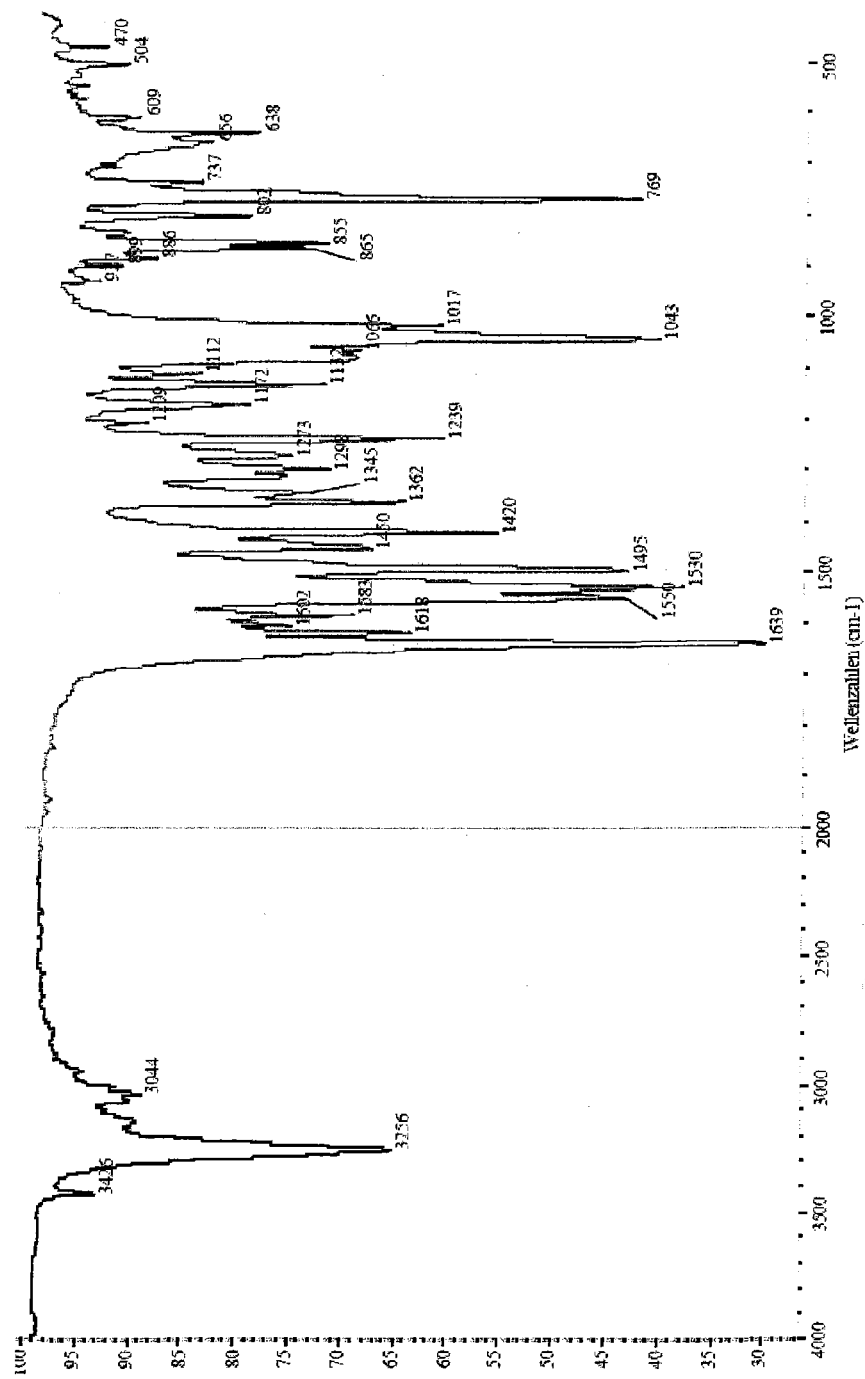
FIGURE 3. FT IR-spectra of form B.

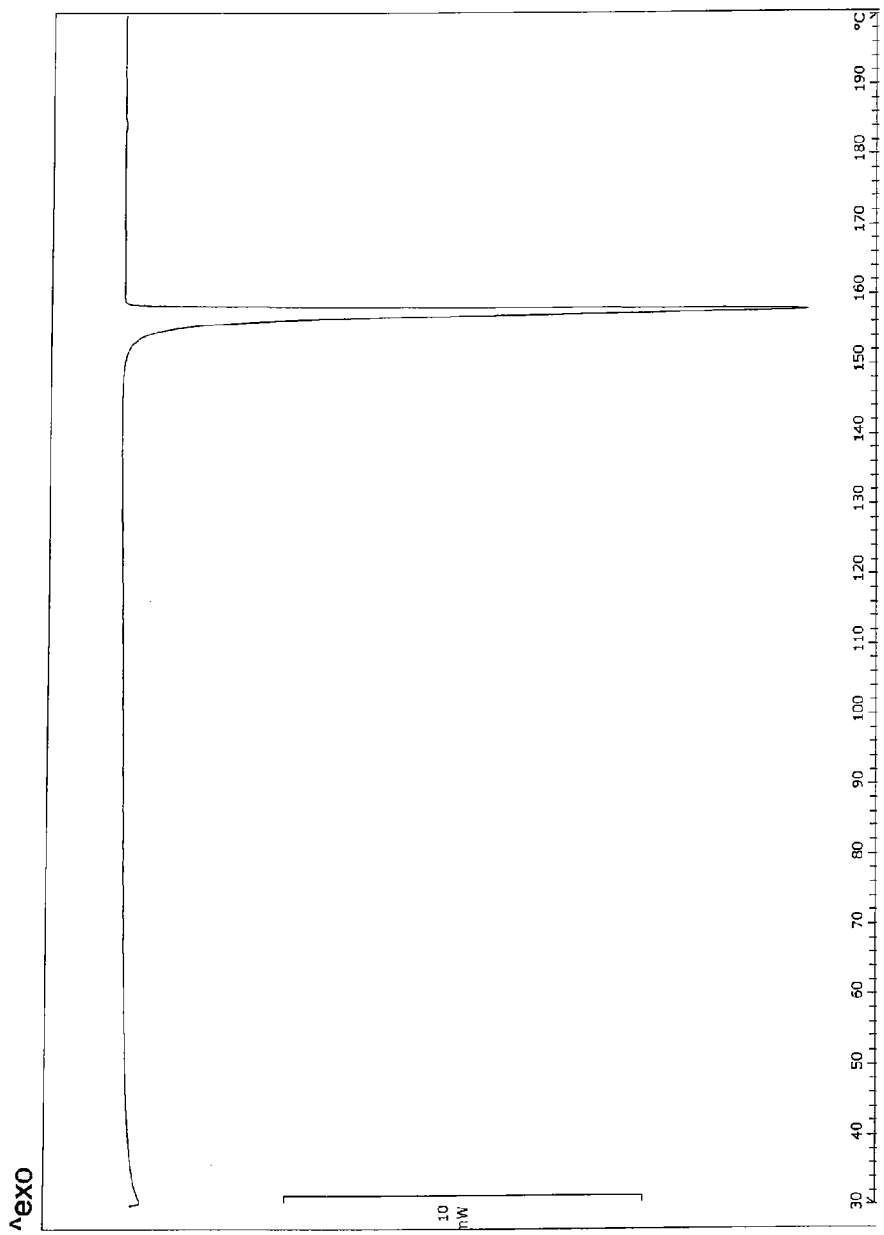
FIGURE 4. DSC of form B.

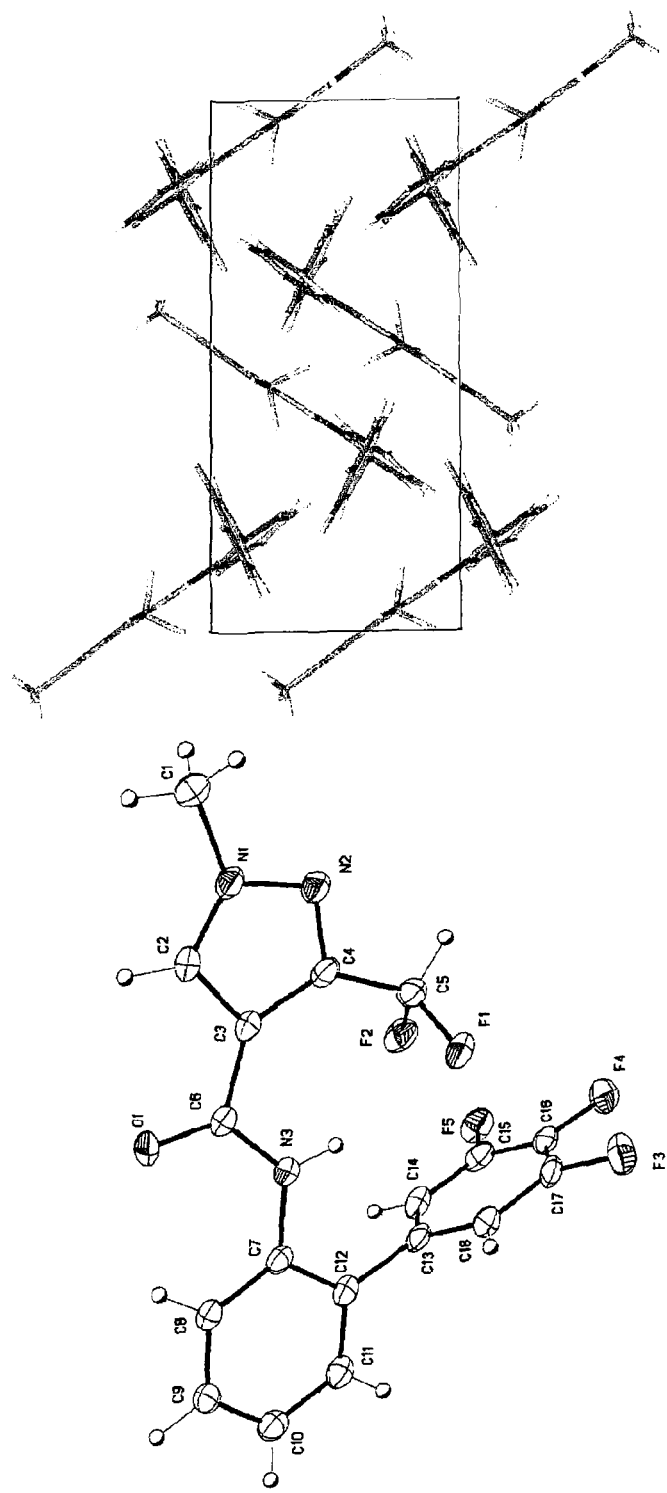
FIGURE 6. Single crystal structure of form A.

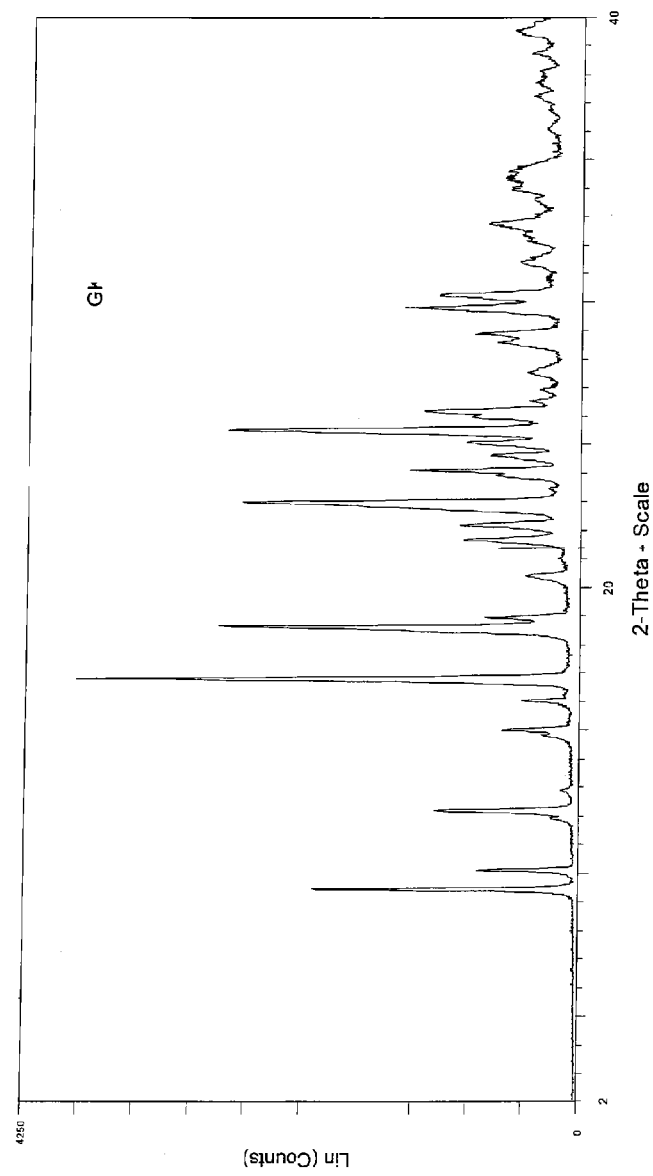
FIGURE 5. Powder X-ray diffractogram of form A.

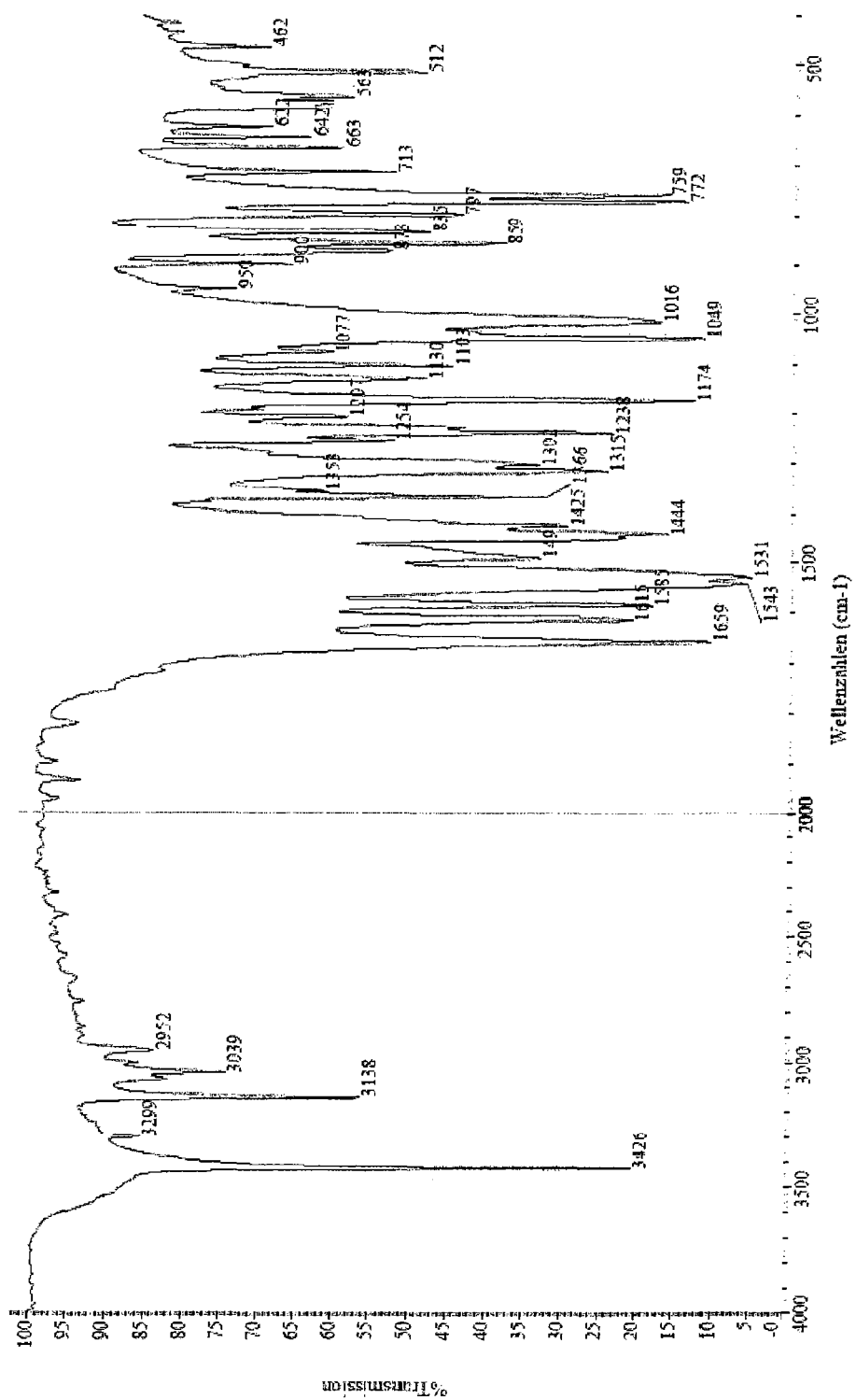
FIGURE 7. FT IR-spectra of form A.

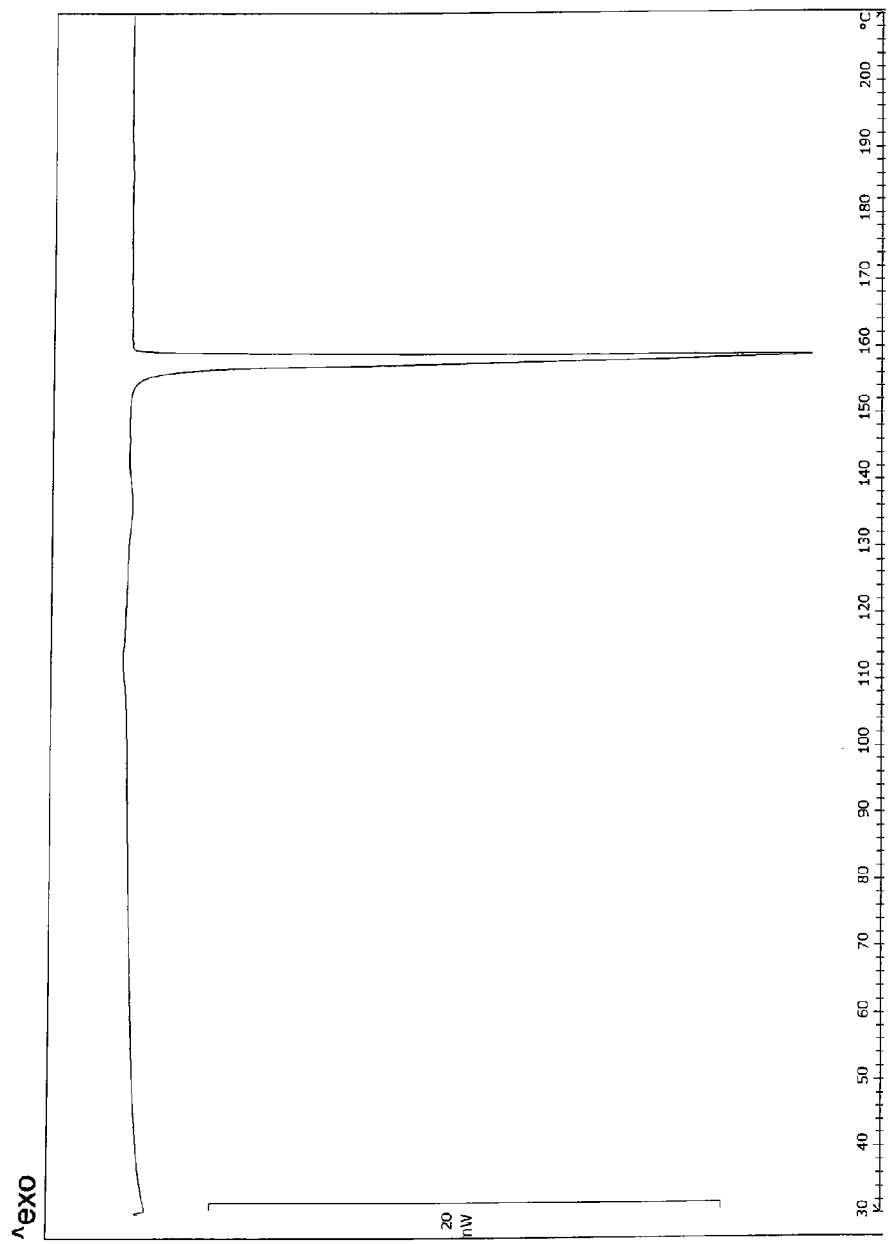
FIGURE 8. DSC-curve of form A with heating rate 2°C/minute.

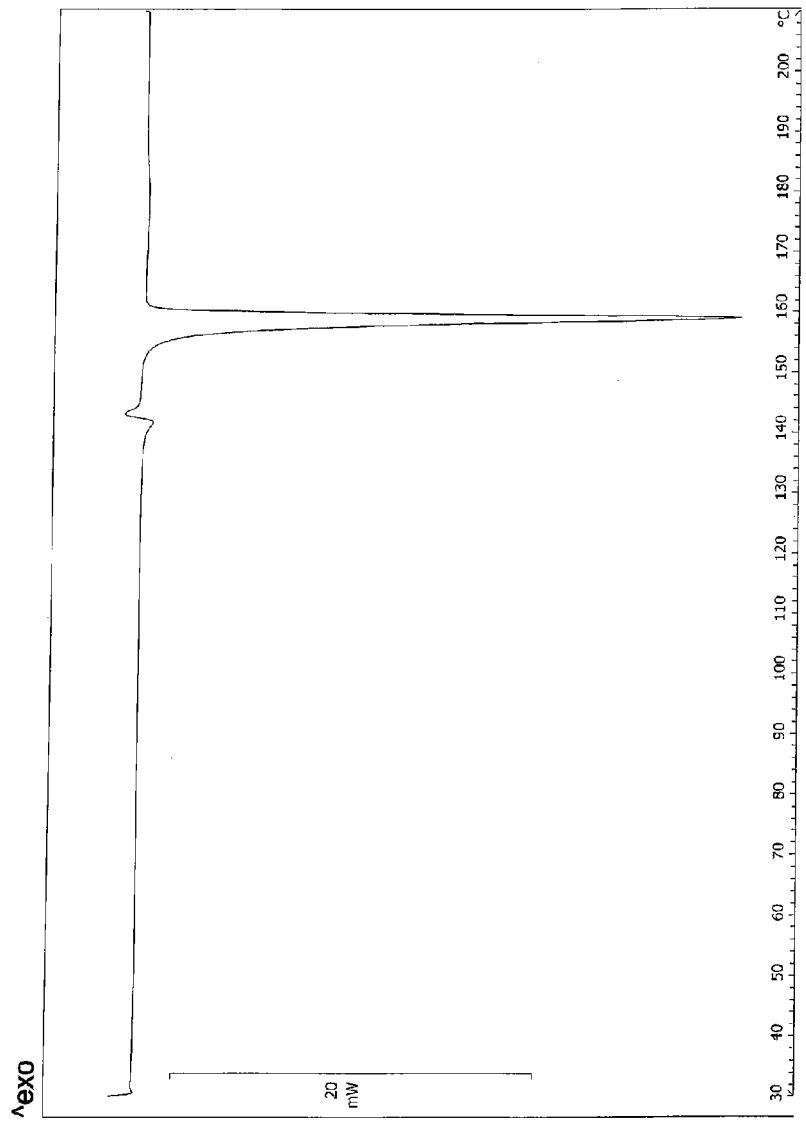
FIGURE 9. DSC-curve of form A with heating rate 5°C/minute.

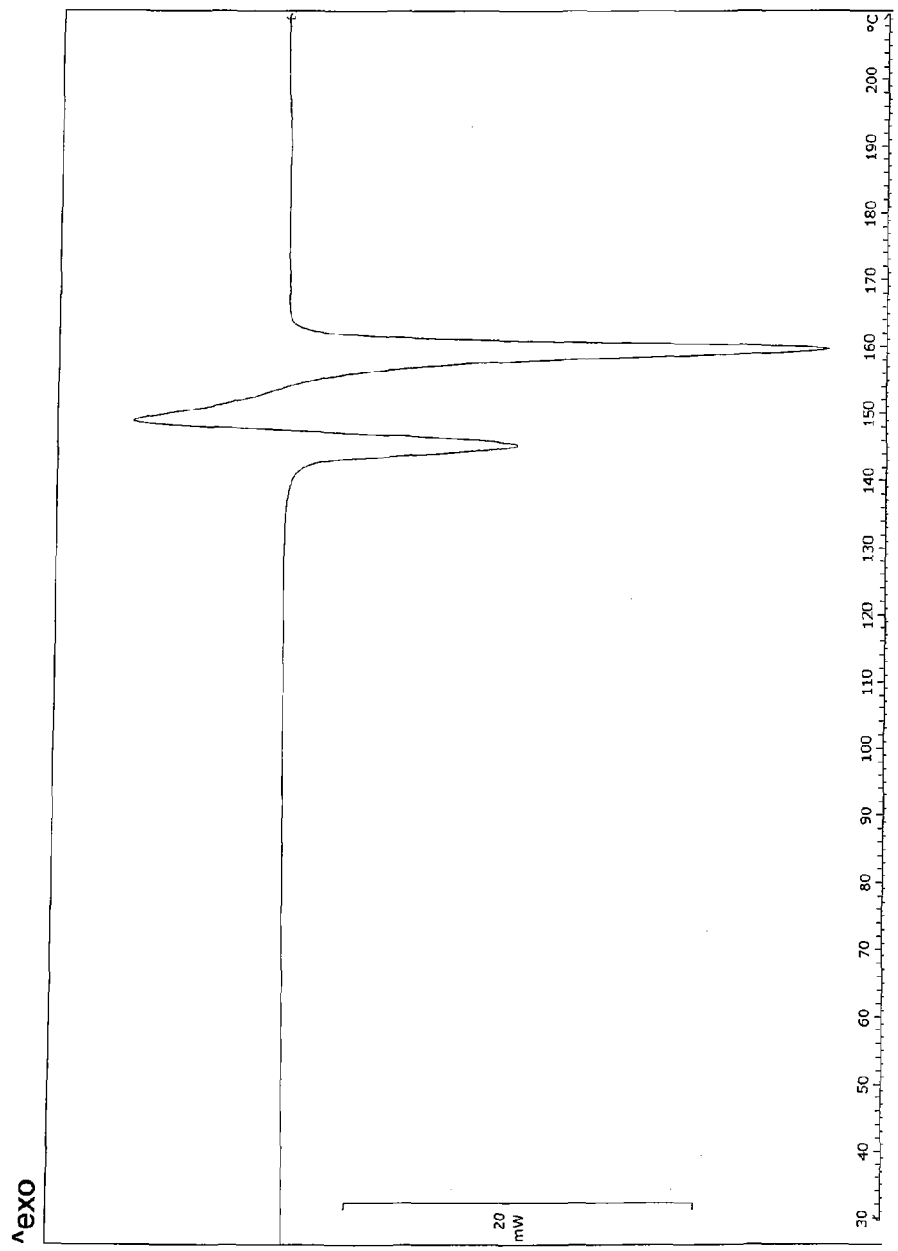
FIGURE 10. DSC trace of form A with heating rate of 10°C/minute.

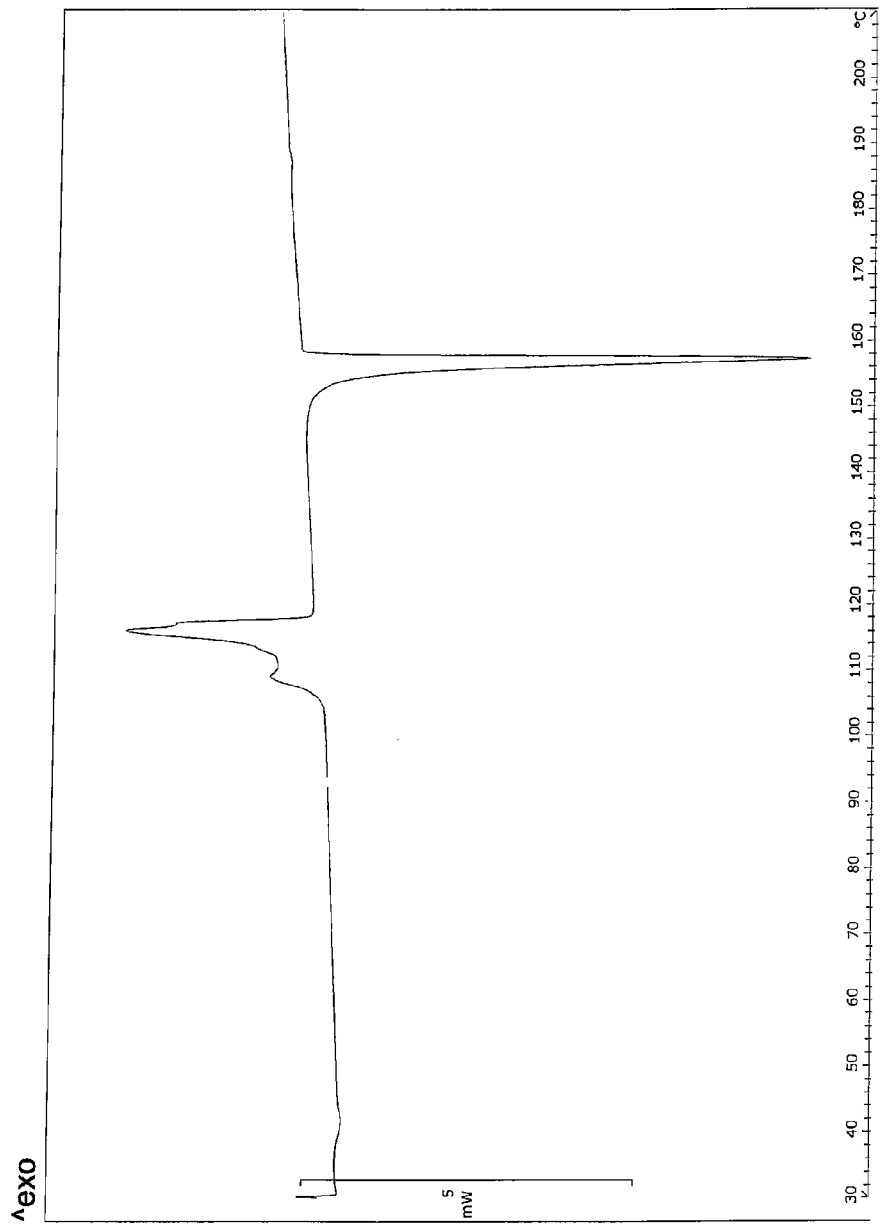
FIGURE 11. DSC trace of amorphous 3-(Difluormethyl)-1-methyl-N -(3',4',5'-trifluor[1,1'-biphenyl]-2-yl)-1H-pyrazol-4-carboxamide with heating rate of 2°C/min.

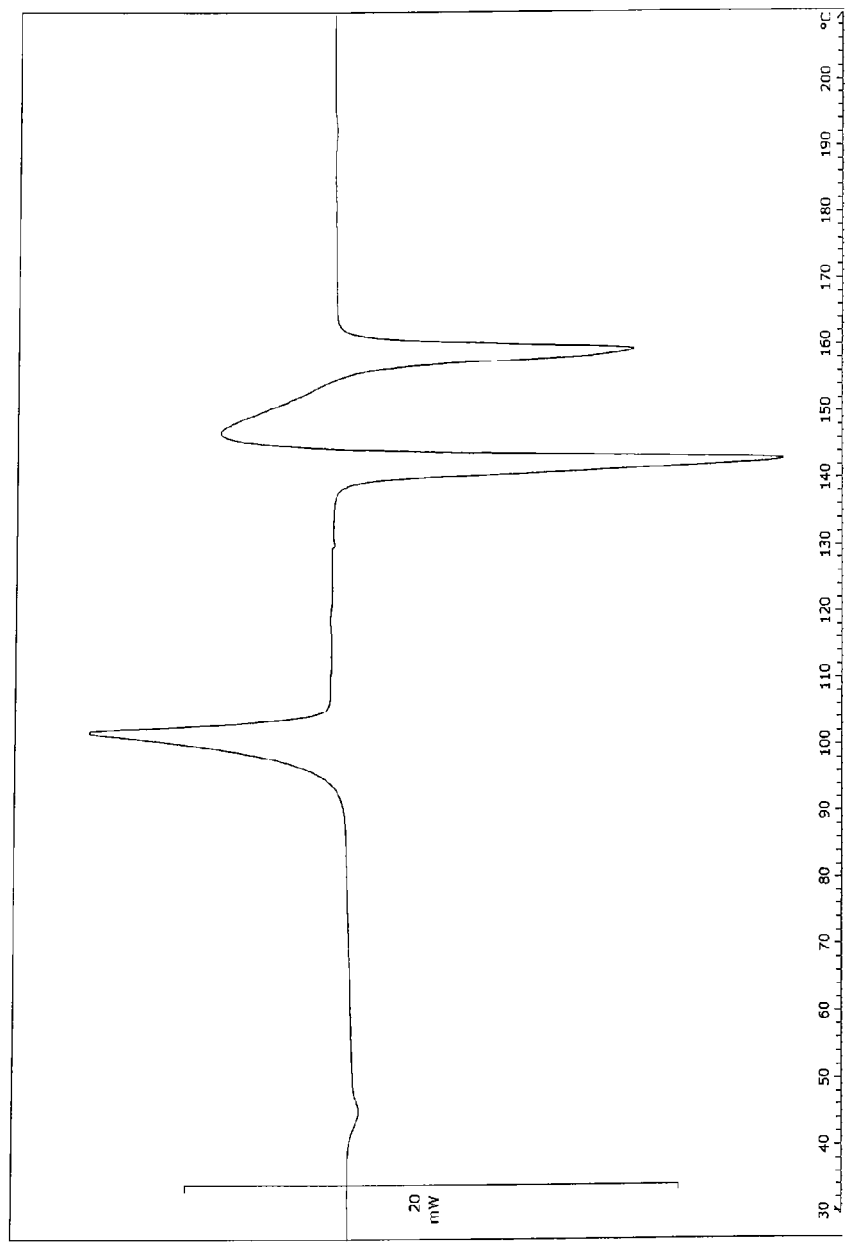
FIGURE 12. DSC trace of amorphous 3-(Difluormethyl)-1-methyl-N -(3',4',5'-trifluor[1,1'-biphenyl]-2-yl)-1H-pyrazol-4-carboxamide with heating rate of 10°C/min.

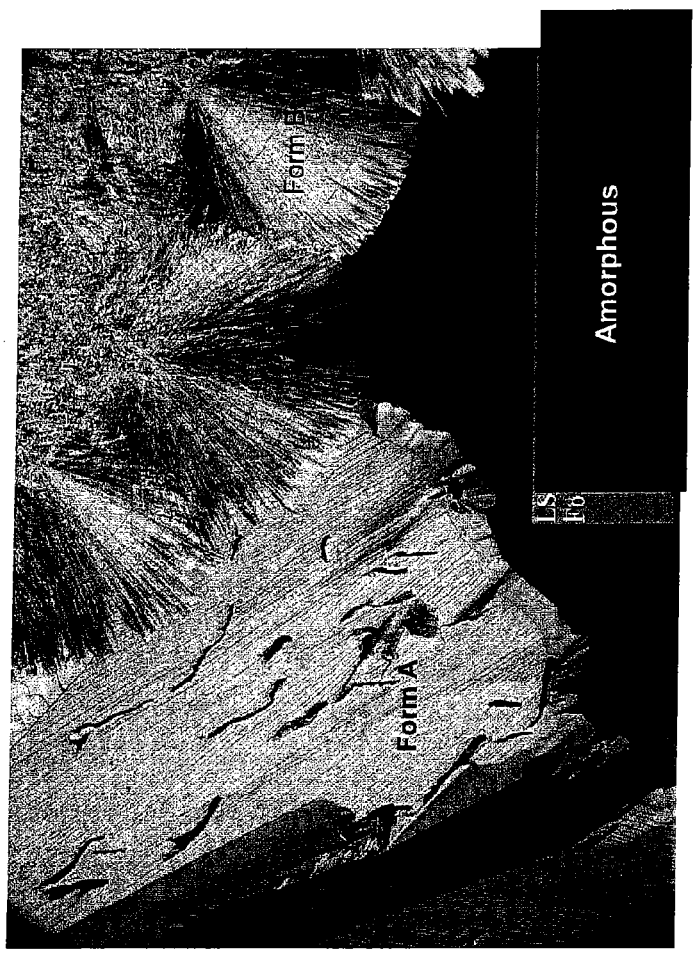
FIGURE 13. Micrograph of a hot stage experiment of the amorphous 3-(Difluormethyl)-1-methyl-N -(3',4',5'-trifluor[1,1'-biphenyl]-2-yl)-1H-pyrazol-4-carboxamide.

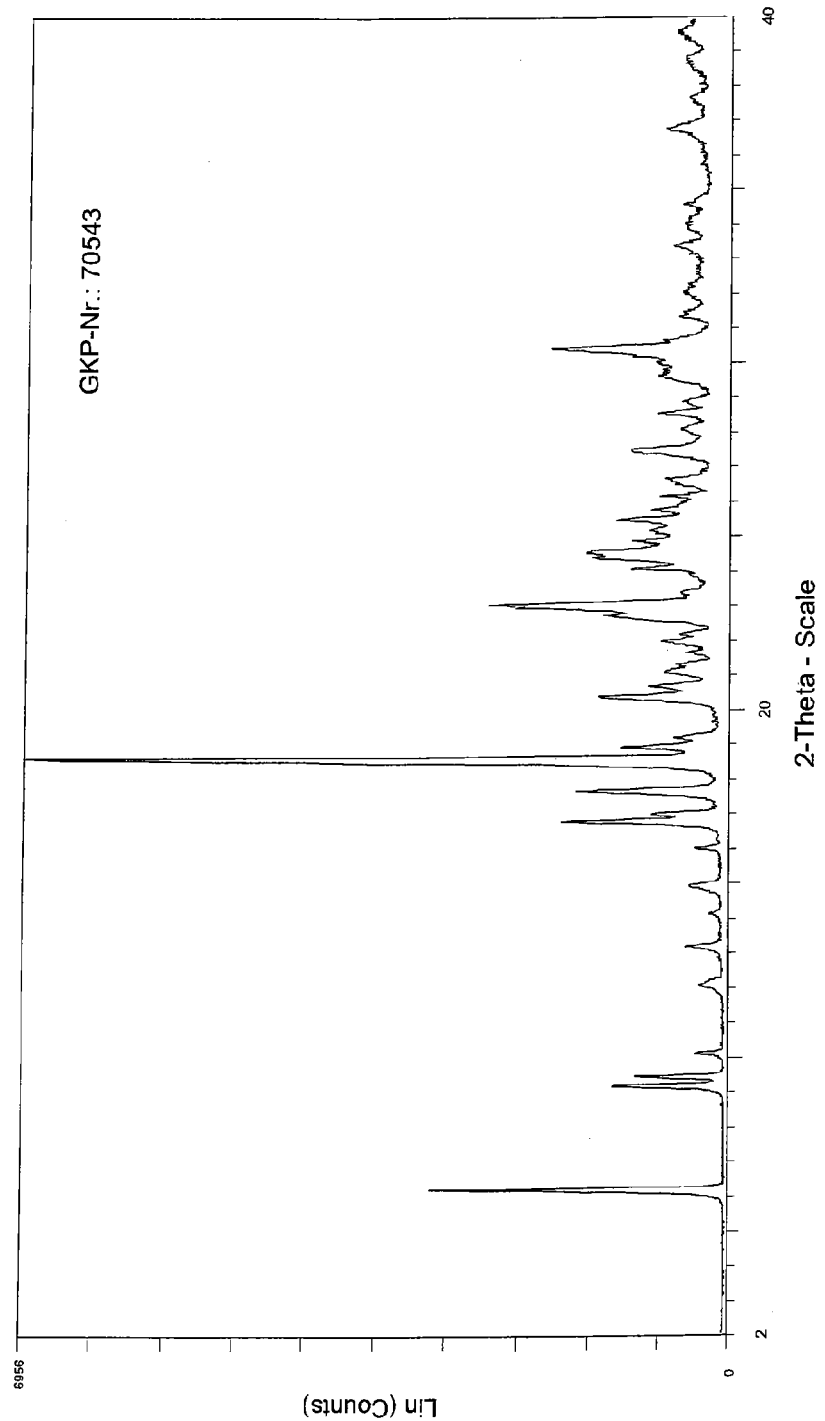
FIGURE 14. Powder X-ray diffractogram of a mixture of form A and form B.

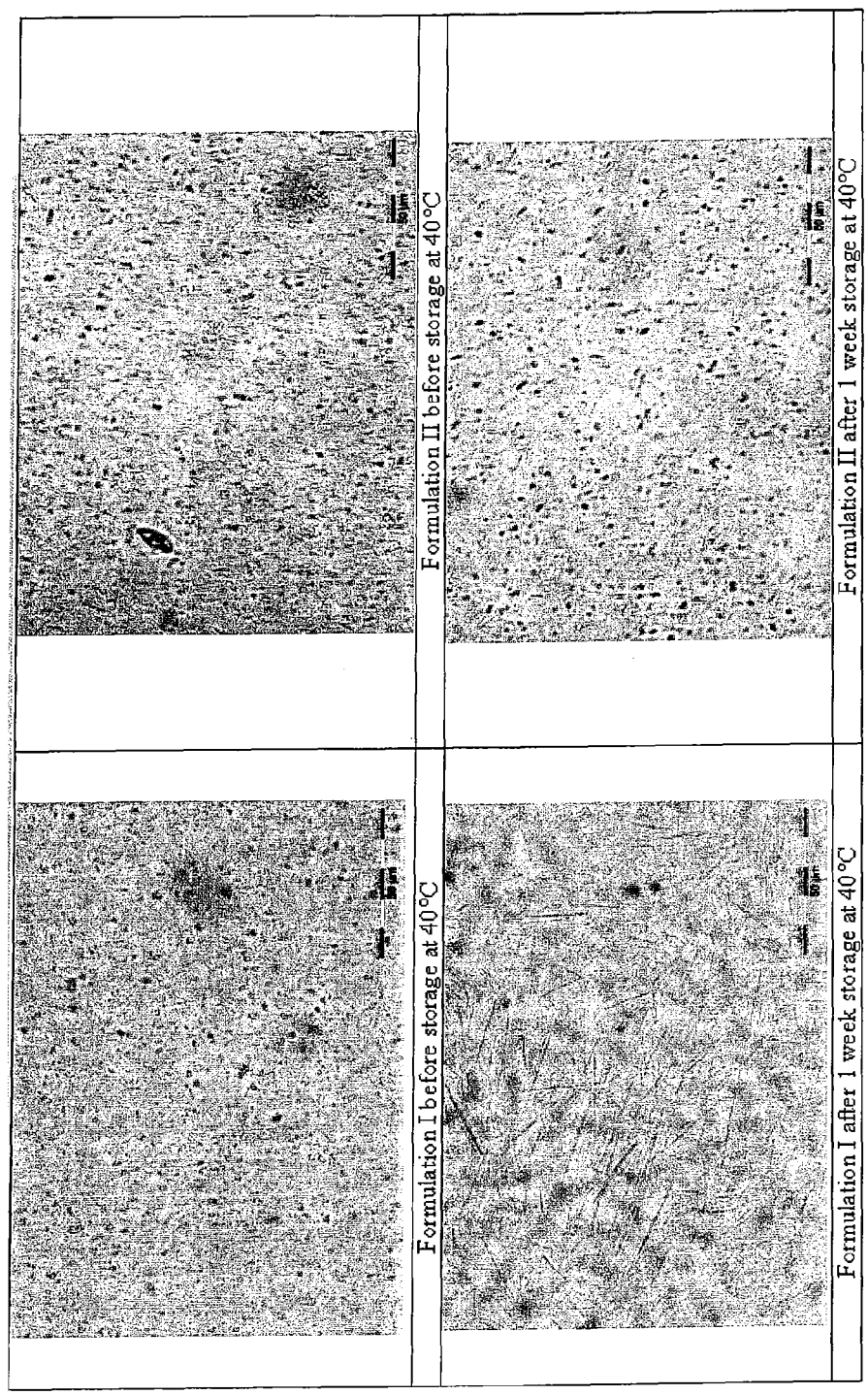
FIGURE 15. Micrographs of stability tests of formulations with form A (formulation I) and form B (formulation II).

CRYSTALLINE FORM OF 3-(DIFLUORMETHYL)-1-METHYL-N-(3',4',5'-TRIFLUOR[1,1'-BIPHENYL]-2-YL)-1H-PYRAZOL-4-CARBOXAMIDE

This application is a National Stage application of International Application No. PCT/EP2008/058785 filed Jul. 7, 2008, the entire contents of which is hereby incorporated herein by reference. This application also claims the benefit under 35 U.S.C. §119 of European Patent Application No. 07112393.9, filed Jul. 12, 2007, the entire contents of which is hereby incorporated herein by reference.

FIELD OF THE INVENTION

The present invention relates to a novel crystalline form of 3-(Difluormethyl)-1-methyl-N-(3',4',5'-trifluor[1,1'-biphenyl]-2-yl)-1H-pyrazol-4-carboxamide. The invention also relates to a process for the production of this crystalline form and formulations for plant protection which contain this crystalline form of 3-(Difluormethyl)-1-methyl-N-(3',4',5'-trifluor[1,1'-biphenyl]-2-yl)-1H-pyrazol-4-carboxamide.

BACKGROUND OF THE INVENTION 3-(Difluormethyl)-1-methyl-N-(3',4',5'-trifluor[1,1'-biphenyl]-2-yl)-1H-pyrazol-4-carboxamide is depicted by the following formula:

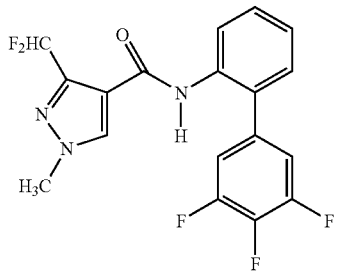

3-(Difluormethyl)-1-methyl-N-(3',4',5'-trifluor[1,1'-biphenyl]-2-yl)-1H-pyrazol-4-carboxamide and a general procedure for its production is known from WO 2006/087343. This procedure yields the compound as an amorphous solid. 3-(Difluormethyl)-1-methyl-N-(3',4',5'-trifluor[1,1'-biphenyl]-2-yl)-1H-pyrazol-4-carboxamide is also disclosed in WO 2007/017416.

For the production of active substances on the industrial scale but also for the formulation of active substances, in many cases knowledge concerning the possible existence of crystalline modifications (also described as crystalline forms or polymorphs) or of solvates of the active substance in question, and knowledge of the specific properties of such modifications and of methods for their preparation are of decisive importance. A range of active substances can exist in several different crystalline but also in amorphous modifications. Polymorphism is the term used in these cases. A polymorph is a solid, crystalline phase of a compound which is characterized from other polymorphs of the compound of interest by a specific, uniform packing and arrangement of the molecules in the solid. Despite ongoing efforts in top research groups around the world, the possible existence or properties of crystalline modifications for an active is not predictable and can thus not be foreseen.

Different modifications of one and the same active substance can have different properties. These include solubility, vapor pressure, dissolution rate, stability against a phase change into a different modification, stability during grinding, suspension stability, optical and mechanical properties, hygroscopicity, crystal form and size, filterability, density, melting point, stability to decomposition, color and sometimes even chemical reactivity or biological activity.

SUMMARY OF THE INVENTION

The applicant's own attempts to convert 3-(Difluormethyl)-1-methyl-N-(3',4',5'-trifluor[1,1'-biphenyl]-2-yl)-1H-pyrazol-4-carboxamide into a crystalline solid by crystallization at first resulted in amorphous products or in a crystalline modification hereafter named as form A, which could only be handled with difficulty and whose formulation stability and stability against phase transformation was uncontrolled and unsatisfactory.

It has now surprisingly been found that by suitable processes one previously unknown crystalline, stable modification of 3-(Difluormethyl)-1-methyl-N-(3',4',5'-trifluor[1,1'-biphenyl]-2-yl)-1H-pyrazol-4-carboxamide which does not display the disadvantages of the so far known amorphous compound or of the crystalline form A is obtained in high purity. This novel modification is described hereafter as form B.

In addition, the inventive crystalline form B is easier to handle than the previously known amorphous 3-(Difluormethyl)-1-methyl-N-(3',4',5'-trifluor[1,1'-biphenyl]-2-yl)-1H-pyrazol-4-carboxamide and its crystalline form A, first of all since during its specific production form B is obtained in the form of discrete crystals or crystallites. Compared to the amorphous compound, to crystalline form A or to mixtures of any of the forms, the pure form B displays increased stability with regard to conversion into another modification. The term "pure form B" should be understood to mean that the proportion of the modification in question, based on the total quantity of 3-(Difluormethyl)-1-methyl-N-(3',4',5'-trifluor[1,1'-biphenyl]-2-yl)-1H-pyrazol-4-carboxamide, is at least 90 wt. % and in particular at least 95 wt. %.

Accordingly, a first object of the present invention relates to the crystalline form B of 3-(Difluormethyl)-1-methyl-N-(3',4',5'-trifluor[1,1'-biphenyl]-2-yl)-1H-pyrazol-4-carboxamide. Also an object is a 3-(Difluormethyl)-1-methyl-N-(3',4',5'-trifluor[1,1'-biphenyl]-2-yl)-1H-pyrazol-4-carboxamide with at least 90 wt. % consisting of the crystalline form B.

BRIEF DESCRIPTION OF THE ILLUSTRATIONS USED TO CLARIFY THE INVENTION

FIG. 1: is an X-ray powder diffractogram of crystalline form B.

FIG. 2: is a single crystal X-ray structure of crystalline form B.

FIG. 3: is a FT Infrared spectrum of crystalline form B.

FIG. 4: is a Differential Scanning Calorimetry (DSC) thermogram of crystalline form B.

FIG. 5: is an X-ray powder diffractogram of crystalline form A.

FIG. 6: is a single crystal X-ray structure of crystalline form A.

FIG. 7: is a FT Infrared spectrum of crystalline form A.

FIGS. 8, 9 and 10 Differential Scanning Calorimetry (DSC) thermograms of crystalline form A with heating rates 2, 5 and 10° C./min, respectively.

FIGS. 11 and 12: are Differential Scanning Calorimentry (DSC) thermograms of amorphous 3-(Difluormethyl)-1-methyl-N-(3',4',5'-trifluor[1,1'-biphenyl]-2-yl)-1H-pyrazol-4-carboxamide with heating rates 2 and 10° C./min respectively.

FIG. 13: is Hot stage microscopy image of conversion of amorphous 3-(Difluormethyl)-1-methyl-N-(3',4',5'-trifluor [1,1'-biphenyl]-2-yl)-1H-pyrazol-4-carboxamide to its crystalline forms A and B (heating rate 5° C./min).

FIG. 14: is an X-ray powder diffractogram of a mixture of crystalline forms A and B.

FIG. 15. are micrographs of formulation tests with crystalline form A (formulation I) and crystalline form B (formulation II).

DETAILED DESCRIPTION OF THE INVENTION

Crystalline Form B

The novel crystalline form B according to the invention can be identified by X-ray powder diffractometry on the basis of its diffraction diagram. Thus an X-ray powder diffraction diagram (FIG. 1) recorded using Cu—Kα radiation (1.54178 Å) at 25° C. shows at least 4, often at least 6, in particular at least 8, and especially all of the reflections quoted in the following table as 2θ values or as interplanar spacings d:

TABLE 1

2θ and d-spacing values of a X-ray diffractogram of crystalline form B.

| 2θ | D [Å] |
|---|---|
| 6.2 ± 0.2 | 14.27 ± 0.07 |
| 9.2 ± 0.2 | 9.62 ± 0.07 |
| 12.1 ± 0.2 | 7.32 ± 0.05 |
| 13.2 ± 0.2 | 6.70 ± 0.05 |
| 14.9 ± 0.2 | 5.92 ± 0.04 |
| 17.0 ± 0.2 | 5.20 ± 0.03 |
| 17.7 ± 0.2 | 5.00 ± 0.02 |
| 18.6 ± 0.2 | 4.76 ± 0.02 |
| 22.0 ± 0.2 | 4.03 ± 0.02 |
| 23.1 ± 0.2 | 3.84 ± 0.02 |
| 26.7 ± 0.2 | 3.33 ± 0.02 |
| 27.6 ± 0.2 | 3.23 ± 0.02 |
| 30.5 ± 0.2 | 2.93 ± 0.02 |

Crystalline form B has a needle like crystal habit. The unit cell parameters and the crystal structure could be determined by a single crystal structure measurement. Crystalline form B exhibits a monoclinic crystal system with space group Pbca. The crystallographical data (measured at (−173)° C.) and most important parameters are summarized in Table 2. A picture of the asymmetric unit and a packing view are further depicted in FIG. 2.

TABLE 2

Crystallographical data and paramters of crystalline form B

| Parameter | Crystalline form B |
|---|---|
| Crystal system | orthorombic |
| Space group | Pbca |
| a | 12.7270(9) Å |
| b | 9.2220(8) Å |
| c | 28.4050(1) Å |
| α | 90 |
| β | 90 |
| γ | 90 |
| Volume | 3333.8(4) Å$^3$ |
| Z | 8 |
| Density (calculated) | 1.519 g/cm$^3$ |
| $R^1$; $\omega R^2$ | 0.058, 0.149 |
| Wavelength | 1.54178 Å | a, b, c = Unit cell axes
α, β, γ = Unit cell angles
Z = Number of molecules in the unitcell Furthermore, as shown in FIG. 3, crystalline form B also exhibits an Infrared (IR) spectrum having characteristic peaks at about 1639 and 3256 cm$^{-1}$. These peaks are carbonyl stretch vibration and stretch vibration of N—H, respectively.

Furthermore as shown in FIG. 4, crystalline form B displays a thermogram with a characteristic melting endotherm in the region of 149 and 160° C. The melting point, determined as the onset of the melting endotherm in a differential scanning calorimetry measurement (FIG. 4), typically lies in the range from about 155° C. to 158° C., in particular in the range from 156 to 157° C. The values quoted here relate to values determined by differential scanning calorimetry, DSC, (open aluminium pan, heating rate 2 K/min). The heat of fusion for crystalline form B lies in the range of 90 J/g.

It should be noted that in the case of the solid state forms of 3-(Difluormethyl)-1-methyl-N-(3',4',5'-trifluor[1,1'-biphenyl]-2-yl)-1H-pyrazol-4-carboxamide, a DSC-measurement and especially a traditional melting point measurement should not be used alone in the identification of the resulted solid state form or crystal modification. Namely, depending on the heating rate and other measuring parameters as well as detection technique of the measurement data, the melting point and DSC measurements of the amorphous form and the crystalline form A can be misinterpreted, leading to an erroneous identification of form B.

The production of crystalline form B of 3-(Difluormethyl)-1-methyl-N-(3',4',5'-trifluor[1,1'-biphenyl]-2-yl)-1H-pyrazol-4-carboxamide according to this invention is effected by crystallization from a solution of 3-(Difluormethyl)-1-methyl-N-(3',4',5'-trifluor[1,1'-biphenyl]-2-yl)-1H-pyrazol-4-carboxamide in a suitable organic solvent. Suitable solvents for the crystallization of form B are alcohols like methanol, ethanol and 2-propanol, acetic acid, cyclic ethers like tetrahydrofurane, aprotic solvents like acetonitrile, nitromethane, dimethylsulfoxide, methyl ethyl ketone, diethyl ketone and methyl isobutyl ketone, as well as aromatic solvents like pyridine, 1,2-dichlorobenzene and toluene.

For this, in a first step i) a solution of 3-(Difluormethyl)-1-methyl-N-(3',4',5'-trifluor[1,1'-biphenyl]-2-yl)-1H-pyrazol-4-carboxamide in one of the aforesaid organic solvents is prepared, and then in a second step ii) crystallization of the compound is effected.

The concentration of 3-(Difluormethyl)-1-methyl-N-(3', 4',5'-trifluor[1,1'-biphenyl]-2-yl)-1H-pyrazol-4-carboxamide in the solution used for the crystallization naturally depends on the nature of the solvent and the solution temperature and often lies in the range from 100 to 800 g/l. Suitable conditions can be determined by the person skilled in the art by routine experiments.

Preferably the solution used for the crystallization contains 3-(Difluormethyl)-1-methyl-N-(3',4',5'-trifluor[1,1'-biphenyl]-2-yl)-1H-pyrazol-4-carboxamide in a purity of at least 85%, often at least 90%, in particular at least 95%, i.e. the content of organic impurities which are not organic solvents is not more than 15 wt. %, often not more than 10 wt. %, and in particular not more than 5 wt. %, based on 3-(Difluormethyl)-1-methyl-N-(3',4',5'-trifluor[1,1'-biphenyl]-2-yl)-1H-pyrazol-4-carboxamide dissolved.

The solution used for the crystallization is preferably essentially free from solvents other than those stated above. In this context, "essentially free" means that the concentration of other solvents in the solution containing 3-(Difluormethyl)-1-methyl-N-(3',4',5'-tri-fluor[1,1'-biphenyl]-2-yl)-1H-pyrazol-4-carboxamide does not exceed 10 wt. %, often 5 wt. %, based on the total quantity of solvent.

The solution of 3-(Difluormethyl)-1-methyl-N-(3',4',5'-trifluor[1,1'-biphenyl]-2-yl)-1H-pyrazol-4-carboxamide can for example be prepared by the following methods:

(1) Dissolution of 3-(Difluormethyl)-1-methyl-N-(3',4',5'-trifluor[1,1'-biphenyl]-2-yl)-1H-pyrazol-4-carboxamide, preferably in a form different from crystalline form B, in one of the aforesaid organic solvents, or (2) Preparation of 3-(Difluormethyl)-1-methyl-N-(3',4',5'-trifluor[1,1'-biphenyl]-2-yl)-1H-pyrazol-4-carboxamide by a chemical reaction and transfer of the reaction mixture, if necessary after removal of reagents and/or side products, into an organic solvent suitable according to the invention.

For the preparation of a solution essentially any known form of 3-(Difluormethyl)-1-methyl-N-(3',4',5'-trifluor[1,1'-biphenyl]-2-yl)-1H-pyrazol-4-carboxamide can be used. Preferably amorphous 3-(Difluormethyl)-1-methyl-N-(3',4',5'-trifluor[1,1'-biphenyl]-2-yl)-1H-pyrazol-4-carboxamide or a mixture of different crystalline modifications or a mixture of amorphous and crystalline 3-(Difluormethyl)-1-methyl-N-(3',4',5'-trifluor[1,1-biphenyl]-2-yl)-1H-pyrazol-4-carboxamide will be used.

The dissolution of 3-(Difluormethyl)-1-methyl-N-(3',4',5'-trifluor[1,1'-biphenyl]-2-yl)-1H-pyrazol-4-carboxamide is usually effected at temperatures in the range from 20 to 130° C. In a preferred embodiment of the invention, the dissolution of 3-(Difluormethyl)-1-methyl-N-(3',4',5'-trifluor[1,1-biphenyl]-2-yl)-1H-pyrazol-4-carboxamide is effected at elevated temperature, in particular at 50° C. at least, and naturally the temperature used for dissolution will not exceed the boiling point of the solvent. The dissolution is often effected at temperatures in the range from 50 to 130° C.

The solution of 3-(Difluormethyl)-1-methyl-N-(3',4',5'-trifluor[1,1'-biphenyl]-2-yl)-1H-pyrazol-4-carboxamide can also be prepared by transferring a reaction mixture obtained by a chemical reaction, which contains the compound, if necessary after removal of reagents and/or side products, into an organic solvent suitable according to the invention. This can be effected in such a manner that the reaction is performed in an organic solvent or solvent mixture which consists at least partly, preferably at least 50 wt. %, of a solvent suitable for the crystallization and, if necessary a workup is performed during which excess reagents and any catalysts present and any unsuitable solvents present are removed. The preparation of a solution of 3-(Difluormethyl)-1-methyl-N-(3',4',5'-trifluor[1,1'-biphenyl]-2-yl)-1H-pyrazol-4-carboxamide by chemical reaction of a suitable precursor of this compound can be effected by analogy to the methods which are described in the state of the art cited at the beginning, to which full reference is hereby made.

The crystallization of form B of 3-(Difluormethyl)-1-methyl-N-(3',4',5'-trifluor[1,1'-biphenyl]-2-yl)-1H-pyrazol-4-carboxamide can be effected as follows, for example by cooling of the solution which contains the dissolved compound, by addition of a solubility-decreasing solvent to the solution which contains dissolved 3-(Difluormethyl)-1-methyl-N-(3',4',5'-trifluor[1,1'-biphenyl]-2-yl)-1H-pyrazol-4-carboxamide, in particular by addition of a nonpolar organic solvent or by addition of water, by slow concentration of a saturated solution which contains dissolved 3-(Difluormethyl)-1-methyl-N-(3',4',5'-trifluor[1,1'-biphenyl]-2-yl)-1H-pyrazol-4-carboxamide and evaporation of the solvent at ambient or reduced pressure (from 1013 to 200 mbar), the solution being supersaturated for at least 10 minutes, preferably 30 minutes, before beginning the crystallization, or by a combination of the aforesaid measures.

The crystallization is as a rule carried out until at least 80 wt. %, preferably at least 90 wt. %, of 3-(Difluormethyl)-1-methyl-N-(3',4',5'-trifluor[1,1-biphenyl]-2-yl)-1H-pyrazol-4-carboxamide used crystallizes out.

In a cooling crystallization the start temperature is typically in between 50° C. and 130° C., preferably in between 80° C. and 110° C. and especially in between 75° C. and 90° C. The start temperature may not be higher than the boiling point of the solvent. The end temperature is in between 70° C. and (−20)° C., preferably from 60° C. to 0° C. and especially from 0° C. to 30° C. The cooling rate is in between 20° C./hour and 0.1° C./hour, preferably from 15° C./hour to 2° C./hour and especially from 10° C./hour to 5° C./hour.

The crystallization of form B can be promoted or accelerated by seeding with seed crystals of form B, for example by adding seed crystals of form B before or during the crystallization.

If seed crystals are added during the crystallization, the quantity thereof is typically 0.001 to 10 wt. %, often 0.005 to 5 wt. %, in particular 0.01 to 1 wt. % and especially 0.05 to 0.5 wt. %, based on the dissolved carboxamide.

If the crystallization is performed in the presence of seed crystals of form B, these are preferably only added at a temperature at which the saturation concentration of 3-(Difluormethyl)-1-methyl-N-(3',4',5'-trifluor[1,1'-biphenyl]-2-yl)-1H-pyrazol-4-carboxamide in the solvent in question has been reached, i.e. at or below that temperature at which the dissolved quantity of 3-(Difluormethyl)-1-methyl-N-(3',4',5'-trifluor[1,1'-biphenyl]-2-yl)-1H-pyrazol-4-carboxamide forms a saturated solution in the solvent in question. The person skilled in the art can determine the temperature dependence of the saturation concentration in a solvent in routine experiments.

Alternatively, the crystallization can also be effected by addition of a nonpolar solvent or by addition of water, for example from 5 to 100 vol. %, in particular 20 to 80 vol. % and especially from 30 to 60 vol. %, based on the volume of the polar organic solvent or solvent mixture used for dissolution of 3-(Difluormethyl)-1-methyl-N-(3',4',5'-trifluor[1,1'-biphenyl]-2-yl)-1H-pyrazol-4-carboxamide. The addition of the nonpolar solvent or the addition of water are preferably effected over a prolonged period, for example over a period from 30 mins to 3 hours, in particular over a period from 40 minutes to 2.5 hours. Often this will be done in such a manner that the nonpolar solvent or water is added until the discernable onset of the crystallization and the mixture thus obtained is then left for a time, during which the crystallization of form B proceeds. If necessary, the mixture can then be cooled for completion of the crystallization.

In particular, the addition of the nonpolar solvent or the addition of water and the addition of seed crystals can be combined.

The addition of the nonpolar solvent can be effected in the form of a pure nonpolar solvent or in the form of a mixture of a nonpolar solvent with a solvent used for the dissolution. Examples of nonpolar solvents are aliphatic and cycloaliphatic hydrocarbons with preferably 5 to 10 carbon atoms such as pentane, hexane, cyclopentane, cyclohexane, isohexane, heptane, cycloheptane, octane, decane or mixtures thereof.

The isolation of form B from the crystallization product, i.e. the separation of form B from the mother liquor, is effected by usual techniques for the separation of solid components from liquids, for example by filtration, centrifugation or by decantation. As a rule, the isolated solid will be washed, for example with the solvent used for the crystallization, with water or with a mixture of the organic solvent used for the crystallization with water. The washing can be effected in one or more steps, washing with water often being used in the last washing step. The washing is typically effected at temperatures below 30° C., often below 25° C. and in particular below 20° C., in order to keep the loss of valuable product as small as possible. Next, crystalline form B obtained can be dried and then supplied for further processing. Often, however, the moist active substance obtained after washing, in particular an active substance moist with water, will be supplied directly for the further processing.

In addition to the crystallization from a solution, form B of 3-(Difluormethyl)-1-methyl-N-(3',4',5'-trifluor[1,1-biphenyl]-2-yl)-1H-pyrazol-4-carboxamide can also be achieved purely by heating the amorphous compound, its crystalline form A, mixtures of these two forms as well as mixtures of form B with any or all the previously known forms.

This process is carried out at a temperature from 80° C. to 154° C., preferably from 100° C. to 140° C. and especially from 105° C. to 120° C., for at least 30 minutes, preferably about 1 hour. The reaction pressure can be from about normal pressure (1013 mbar) to 5 mbar. Preferably, one takes a pressure from 1013 mbar to 200 mbar, especially from 800 mbar to 400 mbar. In this case, the phase transformation takes mostly place through sublimation which is favored by lower pressures.

By means of the crystallization according to the invention, crystalline form B is obtained with a carboxamide content of as a rule at least 90 wt. %, often 94 wt. %, in particular at least 96 wt. %. The content of form B, based on the total quantity of 3-(Difluormethyl)-1-methyl-N-(3',4',5'-trifluor[1,1'-biphenyl]-2-yl)-1H-pyrazol-4-carboxamide, is typically at least 90% and often at least 96%.

The preparation of crude 3-(Difluormethyl)-1-methyl-N-(3',4',5'-trifluor[1,1'-biphenyl]-2-yl)-1H-pyrazol-4-carboxamide for the production of crystalline form B can be effected by the methods described in WO 2006/087343.

The starting material used for preparing crystalline form B can be any form of 3-(Difluormethyl)-1-methyl-N-(3',4',5'-trifluor[1,1'-biphenyl]-2-yl)-1H-pyrazol-4-carboxamide, including amorphous form, crystalline form A and crystalline form B.

In connection with the study and discovery on the crystallization of form B, amorphous 3-(Difluormethyl)-1-methyl-N-(3',4',5'-trifluor[1,1'-biphenyl]-2-yl)-1H-pyrazol-4-carboxamide and its crystalline form A were characterized in detail. Unlike crystalline form B, form A and amorphous 3-(Difluormethyl)-1-methyl-N-(3',4',5'-trifluor[1,1'-biphenyl]-2-yl)-1H-pyrazol-4-carboxamide cannot be stably formulated.

Form A

Crystalline form A of 3-(Difluormethyl)-1-methyl-N-(3',4',5'-trifluor[1,1'-biphenyl]-2-yl)-1H-pyrazol-4-carboxamide can be identified by X-ray powder diffractometry on the basis of its diffraction diagram (FIG. 5). Thus an X-ray powder diffraction diagram recorded using Cu—Kα radiation (1.54178 Å) at 25° C. shows at least 3, often at least 5, and especially all of the reflections quoted in the following table as 2θ values or as interplanar spacings d:

TABLE 3

2θ and d-spacing values of a X-ray diffractogram of crystalline form A.

| 2θ | d [Å] |
|---|---|
| 9.4 ± 0.2 | 9.38 ± 0.07 |
| 10.1 ± 0.2 | 8.78 ± 0.06 |

TABLE 3-continued

2θ and d-spacing values of a X-ray diffractogram of crystalline form A.

| 2θ | d [Å] |
|---|---|
| 12.2 ± 0.2 | 7.28 ± 0.05 |
| 16.0 ± 0.2 | 5.52 ± 0.05 |
| 16.8 ± 0.2 | 5.27 ± 0.05 |
| 21.7 ± 0.2 | 4.10 ± 0.03 |
| 23.0 ± 0.2 | 3.87 ± 0.03 |
| 25.5 ± 0.2 | 3.49 ± 0.02 |
| 29.8 ± 0.2 | 2.99 ± 0.02 |
| 32.8 ± 0.2 | 2.72 ± 0.02 |

Crystalline form A has a block like crystal habit. The unit cell parameters and the crystal structure could be determined by a single crystal structure measurement. Form A exhibits a monoclinic crystal system with space group P2(1)/c. The crystallographic data (measured at (−173)° C.) and most important parameters are summarized in Table 4. A picture of the asymmetric unit and a packing view are further depicted in FIG. 6.

TABEL 4

Crystallographical data and paramters of crystalline form A

| Parameter | Form A |
|---|---|
| Crystal system | monoclinic |
| Space group | P2(1)/c |
| a | 11.639(2) Å |
| b | 17.067(2) Å |
| c | 8.5951(1) Å |
| α | 90 |
| β | 108.95(1)° |
| γ | 90 |
| Volume | −1614.8 Å$^3$ |
| Z | 4 |
| Density (calculated) | 1.57 g/cm$^3$ |
| R$^1$; ωR$^2$ | 0.087, 0.184 |
| Wavelength | 1.54178 Å | a, b, c = Unit cell axes
α, β, γ = Unit cell angles
Z = Number of molecules in the unitcell Furthermore, as shown in FIG. 7, form A also exhibits an Infrared (IR) spectrum having characteristic peaks at about 1659, 3138 and 3426 cm$^{-1}$. These peaks are carbonyl stretch vibration (1659 cm$^{-1}$) and stretch vibration of N—H (3138 and 3426 cm$^{-1}$), respectively.

The melting point measurement of form A is complicated and very easily results incorrectly as the melting point value of crystalline form B. This is due to the fact that during a melting process of block like crystals of form A, a phase transformation takes place and in a DSC (differential scanning calorimetry) measurement the melting endotherm of form A is easily masked by the exotherm related to phase transformation and crystallization of the newly identified form B. The heating rate is a crucial parameter in such systems and vastly different DSC traces are obtained at different heating rates (see FIGS. 8, 9 and 10). With a very low heating rate (2° C./min) the melting and phase transformation of form A to form B can not be detected and essentially only the melting peak of form B is depicted. With faster heating rates (see FIGS. 9 and 10) the melting endotherm of form A becomes visible and can clearly be seen in FIG. 10 with a heating rate of 10° C./min. In FIG. 10, the melting of form A is followed right by crystallization of form B and finally the melting of form B. Other experimental factors influencing the quality of the DSC measurement of form A include sample mass, particle size, the presence of impurities, the shape of the crystalline particles and the presence of nuclei or seeds of various polymorphs (see also J. Bernstein, Polymorphism in Molecular Crystals, IUCR Monographs of crystallography, Oxford University Press, 2002, pp. 104-111).

Form A displays a thermogram with a characteristic melting peak in the region of 138 and 145° C. The peak maximum typically lies in the range from 142 to 144° C. The melting point, determined as the onset of the melting peak, typically lies in the range from about 142° C. to 144° C. The values quoted here relate to values determined by differential calorimetry (differential scanning calorimetry: DSC, open aluminum pan, heating rate 10 K/min).

Crystalline form A of 3-(Difluormethyl)-1-methyl-N-(3',4',5'-trifluor[1,1'-biphenyl]-2-yl)-1H-pyrazol-4-carboxamide can be prepared by fast evaporation crystallizations from solvents like dichloromethane, toluene and monochlorobenzene or by fast cooling crystallizations from the same solvents.

The starting material used for preparing form A can be any form of 3-(Difluormethyl)-1-methyl-N-(3',4',5'-trifluor[1,1'-biphenyl]-2-yl)-1H-pyrazol-4-carboxamide, including amorphous form, crystalline form A and crystalline form B.

Amorphous Carboxamide

The amorphous form of 3-(Difluormethyl)-1-methyl-N-(3',4',5'-trifluor[1,1-biphenyl]-2-yl)-1H-pyrazol-4-carboxamide may be characterized by, for example, X-ray powder diffraction. In a X-ray powder diffractogram the amorphous form gives only a background signal with no significant signals typical for crystalline material.

In another aspect, the amorphous form converts at room temperature slowly to crystalline form A or typically to mixtures of form A and form B. The conversion can not be easily controlled, but the conversion can be directed towards form B by using elevated storage temperatures. The phase transformation can be seen for example in a DSC measurement or under a hot stage microscope.

The amorphous form of 3-(Difluormethyl)-1-methyl-N-(3',4',5'-trifluor[1,1-biphenyl]-2-yl)-1H-pyrazol-4-carboxamide can be prepared by precipitation or evaporation of an unpure material (purity less than 70%) or melting any of its crystalline forms and cooling the melt down to room temperature. During heating the amorphous form crystallizes to form A or form B or mixtures of these two forms. The conversion can be accelerated by heating or high moisture content or direct contact with solvents.

In a typical melting point measurement the conversion of amorphous form to one of the crystalline forms A or B or to a mixture of these two forms, takes place in between 95 to 130 degrees (see FIGS. 10 and 11). Similar to the DSC measurement of crystalline form A the DSC measurement of the amorphous form is highly dependent on the measurement parameters. At a heating rate typical for a melting point measurement (10° C./min, see FIG. 11) the peak maxima for the crystallization process is for example at about 115° C. In a visual or automatic melting point measurement this point can be misinterpreted as a melting point. The risk for misinterpretation is highly promoted by the fact that the amorphous form of 3-(Difluormethyl)-1-methyl-N-(3',4',5'-trifluor[1,1'-biphenyl]-2-yl)-1H-pyrazol-4-carboxamide sublimes readily at this temperature giving a melting like visual effect.

This description, together with the thermal behavior description of the crystalline form A demonstrates that thermal methods and melting point measurements can not be used to decisively show the actually present modification at room temperature. When thermal methods are used in characterization of the solid state forms of 3-(Difluormethyl)-1-methyl-N-(3',4',5'-trifluor[1,1'-biphenyl]-2-yl)-1H-pyrazol-4-carboxamide it is crucial to use also comparative method (for example powder diffraction or FT IR spectrometry).

The amorphous form of 3-(Difluormethyl)-1-methyl-N-(3',4',5'-trifluor[1,1'-biphenyl]-2-yl)-1H-pyrazol-4-carboxamide can also be obtained via solution crystallization, especially if impurities are present.

The starting material used for preparing the amorphous form can be any form of 3-(Difluormethyl)-1-methyl-N-(3',4',5'-trifluor[1,1'-biphenyl]-2-yl)-1H-pyrazol-4-carboxamide, including crystalline form A and crystalline form B as well as the amorphous form itself.

Mixtures of Form A and Form B with Amorphous Carboxamide

Crystalline form B sometimes appear in mixture with form A (FIG. 14). However, said mixtures are unfavourable for formulation purposes. By using seeding with crystals of form B, one can significantly promote the formation of form B, for example in toluene.

A Detailed Description of the Figures

The following illustrations and examples serve to illustrate the invention and should not be regarded as limiting.

FIG. 1 shows a characteristic X-ray powder diffraction diagram of crystalline form B. The X-ray diffractrion diagram of form B was recorded with a Bruker-AXS Co. D-5000 diffractometer in reflection geometry in the range from $2\theta=2°-40°$ with a step width of 0.02° using Cu—K$\alpha$ radiation (1.54178 Å) at 25° C.

FIG. 2 shows a drawing of the single crystal structure of form B. The asymmetric unit is depicted on the left side and the crystal packing on the right. The X-ray diffraction data for crystalline form B were collected at the synchrotron SLS (Villingen, Switzerland) at the PX beamline. The structure was solved by using direct methods, refined, and expanded by using Fourier techniques with the SHELX software package (G. M. Sheldrick, SHELX-97, University of Goettingen, 1997).

FIG. 3 shows a FT IR-spectrum of crystalline form B. The sample was prepared as KBr-pellets and the spectrum was recorded in a FT IR-spectrometer (e.g. Nicolet Magna) in transmission mode (T=25° C.; 32 scans; resolution 4 cm$^{-1}$).

FIG. 4 shows a DSC trace of form B with the maximum of the melting endotherm at about 157° C. measured using a Mettler Co. Mettler Toledo DSC 25 with a heating rate of 10° C./min in the range from 30° C. to 200° C. The sample weight was 5 to 10 mg.

FIG. 5 shows an X-ray powder diffraction diagram of crystalline form A. The X-ray diffraction diagram of form A was recorded with a Bruker-AXS Co. D-5000 diffractometer in reflection geometry in the range from $2\theta=2°-40°$ with a step width of 0.02° using Cu—K$\alpha$ radiation (1.54178 Å) at 25° C.

FIG. 6 shows a drawing of the single crystal structure of form B. The asymmetric unit is depicted on the left side and the crystal packing on the right. The X-ray diffraction data for crystalline form A were collected on a Bruker AXS CCD Detector, using graphite-monochromated Cu—K$\alpha$ radiation (1.54178 Å). The structure was solved by using direct methods, refined, and expanded by using Fourier techniques with the SHELX software package (G. M. Sheldrick, SHELX-97, University of Goettingen, 1997).

FIG. 7 shows a FT IR-spectrum of crystalline form B. The sample was prepared as KBr-pellets and the spectrum was recorded in a FT IR-spectrometer (e.g. Nicolet Magna) in transmission mode (T=25° C.; 32 scans; resolution 4 cm$^{-1}$).

FIGS. 8, 9 and 10 show two significantly different DSC-traces of form A. FIG. 8 is a measurement with 2° C./min heating rate and shows only a melting at about 156° C. In this diagram the melting of form A is actually masked with the simultaneous crystallization of form B. The melting of form A can, however, already be detected in the 5° C./min measurement (FIG. 9) and very well in the 10° C./min measurement (FIG. 10). The latter shows at about 145° C. the melting endotherm of form A, which is followed by instant crystallization exotherm to form B and finally with the melting endotherm of form B. The DSC-traces were measured with a Mettler Co. Mettler Toledo DSC 25 with heating rates of 2, 5 and 10 K/min in the range from 30° C. to 200° C. The sample weight was 5 to 10 mg.

FIGS. 11 and 12 show DSC-thermograms of amorphous 3-(Difluormethyl)-1-methyl-N-(3',4',5'-trifluor[1,1'-biphenyl]-2-yl)-1H-pyrazol-4-carboxamide with heating rates of 2K/min and 10K/min respectively. FIG. 11 first shows the crystallization exotherm of the amorphous compound to crystalline form A, form B or mixtures of these two forms at about 100-120° C. The melting peak of form A can not be seen, whereas the melting peak of form B is present. Due to the possible phase transformation from crystalline form A to form B and the masking effects at slow heating rates (see description of FIGS. 7 and 8) no conclusion concerning the crystalline form present is possible based on only this measurement. In FIG. 12 (heating rate of 12K/min) the crystallization of amorphous form can be seen. After this the DSC is similar to that of form A with a heating rate of 10K/min, giving first melting of form A, followed by crystallization of form B and then melting of form B. The DSC-traces were measured with a Mettler Co. Mettler Toledo DSC 25 with a heating rate of 10K/min in the range from 25° C. to 140° C. The sample weight was 5 to 10 mg.

FIG. 13 shows an X-ray powder diffraction diagram of a mixture of crystalline forms A and B. The X-ray diffraction diagram of the mixture of forms A and B was recorded with a Bruker-AXS Co. D-5000 diffractometer in reflection geometry in the range from 2θ=2°-40° with a step width of 0.02° using Cu—Kα radiation (1.54178 Å) at 25° C.

FIG. 14 shows a Hot stage microscopy picture of a heating experiment of amorphous 3-(Difluormethyl)-1-methyl-N-(3',4',5'-trifluor[1,1'-biphenyl]-2-yl)-1H-pyrazol-4-carboxamide. This heating experiment was performed on an amorphous film (black parts in the picture) with a heating rate of 5° C./min. At the time of the picture the temperature was 115° C. The simultaneous crystallization of the amorphous form to form A and form B can be clearly seen. The measurement was carried out on a Mettler hot stage.

FIG. 15 shows micrographs of formulation tests with form A (formulation I) and form B (formulation II).

The present invention is further illustrated by the following examples.

Example 1

Preparation of Crystalline form B of 3-(Difluormethyl)-1-methyl-N-(3',4',5'-trifluor[1,1'-biphenyl]-2-yl)-1H-pyrazol-4-carboxamide by Crystallization from a Reaction Mixture 9.55 kg 3',4',5'-trifluoro[1,1'-biphenyl]-2-yl-amine (I) were dissolved in 51.4 kg and 6 kg pyridine were added. The mixture was stirred at 45° C. and 8.3 kg 3-(difluoromethyl)-1-methyl-1H-pyrazole-4-carbonyl chloride (II) were dosed during one hour. Due to the exothermic nature of the reaction, the temperature raised to 55° C. Post-reaction by stirring for 1 hour at 55° C. followed. Three extractions at 85° C. with 16 liter hydrochloric acid (5%), 14 liter sodium hydrogen carbonate (8%), and 14 liter deionized water followed. The resulting clear solution in toluene was cooled from 85° C. with a rate of 10° C. per hour to 0° C. Around 75° C., the first turbidity was observed, and at 75° C. and 73° C., respectively, the batch was seeded with 10 g 3-(difluoromethyl)-1-methyl-N-(3',4',5'-trifluoro[1,1'-biphenyl]-2-yl)-1H-pyrazole-4-carboxamide (III) each (>98% form B). The resulting slurry was filtered at 0° C. over a process filter and the filter cake was washed with 10 kg toluene at 0° C. After drying in the drying cabinet at 80° C. and 20 mbar for 12 hours, 13.5 kg 3-(difluoromethyl)-1-methyl-N-(3',4',5'-trifluoro[1,1'-biphenyl]-2-yl)-1H-pyrazole-4-carboxamide (III) of >99.5% purity (GC, HPLC, NMR) was isolated. Using powder diffractometry (PXRD) and Fourier-Transform solid state infrared spectrometry (FT-IR) it was proven that the material consists to >98% of form B.

Example 2

Preparation of Crystalline form B by Crystallization from an Organic Solvent with Cooling:

615 g of 3-(difluoromethyl)-1-methyl-N-(3',4',5'-trifluoro[1,1-biphenyl]-2-yl)-1H-pyrazole-4-carboxamide was dissolved at 85° C. in 2.5 l of boiling toluene in a test vessel. The solution was cooled down from 85° C. to 25° C. with a heating rate of 1° C. per hour. No stirring was applied. The long needle like crystals (crystal length even 1-2 cm) were separated by decanting. A single crystal X-ray structure measurement showed that the crystal modification was form B.

Example 3

Preparation of form B by Crystallization from an Organic Solvent by Evaporation:

A saturated solution of about 1 g of 3-(difluoromethyl)-1-methyl-N-(3',4',5'-trifluoro[1,1'-biphenyl]-2-yl)-1H-pyrazole-4-carboxamide (purity >95%) in methanol was prepared in a test vessel close to the boiling point of the solvent. The test vessel was placed at room temperature with a pierced lid on, allowing the solvent to slowly evaporate. In this manner, 3-(difluoromethyl)-1-methyl-N-(3',4',5'-trifluoro[1,1'-biphenyl]-2-yl)-1H-pyrazole-4-carboxamide was obtained within 2 weeks in the form of crystals, which were isolated and analyzed by X-ray powder diffractometry (XRD) and differential scanning calorimetry (DSC). On the basis of the characteristic reflections, form B was identified. The same experiment, resulting as form B, could be repeated also in ethanol, 2-propanol, acetic acid, tetrahydrofurane, acetonitrile, nitromethane, dimethyl-sulfoxide, methylethyl ketone, methyl isobutyl ketone, pyridine, and toluene.

Example 4

Preparation of Form B by Crystallization from an Organic Solvent by Evaporation 1 g of form A was dissolved in 20 ml of acetophenone at 100° C. in a round bottomed flask. The solvent was evaporated by applying a nitrogen flow on the solution surface. After all solvent was evaporated the crystalline sample was analyzed to be form B by powder diffractometry (XRD). The same experiment could also be carried out with 1,2-dichlorobenzene and diethyl ketone.

Example 5

Preparation of Pure form B by Heating:

2 kg 3-(difluoromethyl)-1-methyl-N-(3',4',5'-trifluoro[1,1'-biphenyl]-2-yl)-1H-pyrazole-4-carboxamide, that according to X-ray powder diffractometry contained >10% of form A, was heated in an oven at 115° C. under 800 mbar for 16 hours. The resulted solid was analyzed (by PXRD and DSC) to be >98% pure form B.

Example 6

Preparation of Pure Form B by Heating:

1 g of pure form A was heated in an oven at 110° C. under normal pressure for 24 hours. The resulted solid was analyzed (by X-ray diffraction and DSC) to be >98% pure form B.

Comparative Example 7

Preparation of Form A by Crystallization from toluene and monochlorobenzene Under Reduced Pressure (Not According to Invention):

5 g of 3-(difluoromethyl)-1-methyl-N-(3',4',5'-trifluoro[1,1'-biphenyl]-2-yl)-1H-pyrazole-4-carboxamide (purity >95%) was dissolved in 50 ml of monochlorobenzene in a round bottom flask at 100° C. The solvent was evaporated under reduced pressure by a standard laboratory rotavapor at 70° C. After all of the solvent was evaporated the resulted solid was analyzed by X-ray powder diffractometry (XRD). On the basis of the characteristic reflections, crystalline form A was identified.

Comparative Example 8

Preparation of Form A by Crystallization from Dichloromethane (Not According to Invention):

200 mg of form A was dissolved in 3 ml of dichloromethane at about 35° C. in a small glass tube. The solvent was left to evaporate under normal pressure at 30° C. The experiment resulted as block like crystals that we confirmed to be that of form A by single crystal X-ray measurement.

Comparative Example 9

Preparation of Amorphous Carboxamide:

A sample of 1 g of crystalline form A was placed in an oven in a round bottom flask at the temperature of 160° C. for 20 minutes. The melt of 3-(difluoromethyl)-1-methyl-N-(3',4',5'-trifluoro[1,1'-biphenyl]-2-yl)-1H-pyrazole-4-carboxamide was then brought to room temperature and left to cool. An amorphous film like material resulted giving no diffraction pattern in a powder diffraction measurement.

Comparative Experiments Yielding as Mixtures of Forms A and B

Comparative Example 10

A saturated solution of about 300 mg of 3-(difluoromethyl)-1-methyl-N-(3',4',5'-trifluoro[1,1'-biphenyl]-2-yl)-1H-pyrazole-4-carboxamide (purity >95%) in diethyl ether was prepared at room temperature. The solvent was left to evaporate at 30° C. from an open glass tube. The resulted crystalline material was analyzed by powder X-ray diffractometry to be a mixture of form A and B (see FIG. 10 for the characteristic XRD).

Comparative Example 11

An experiment similar to Example 10 was carried out from toluene. The solvent evaporation took several days, after which the solid crystalline sample was analyzed. According to powder X-ray diffractometry it contained a mixture of form A and B.

Example 12 and 13

Slurry Examples Proving the Stability of Form B:

The form in question or mixtures of different forms of 3-(difluoromethyl)-1-methyl-N-(3',4',5'-trifluoro[1,1'-biphenyl]-2-yl)-1H-pyrazole-4-carboxamide were suspended in water at 30° C. The mixture was kept at this temperature and stirred with a magnetic stirrer.

Example 12: After 1 day under these conditions the amorphous form had converted (based on XRD analysis) into form B.

Example 13: After 2 days under these conditions crystalline form A had converted (based on XRD analysis) into form B.

Examples 14 and 15

Formulation Examples Proving the Stability of Crystalline Form B:

The stability of the crystalline forms was tested by formulating form A or form B according to examples 1 and 2 and analyzing the formulation stability in the form of sedimentation, particle size growth and change in crystalline modification.

Example 14

SC Formulation Containing Crystalline Form A of 3-(difluoromethyl)-1-methyl-N-(3',4',5'-trifluoro[1,1'-biphenyl]-2-yl)-1H-pyrazole-4-carboxamide:

An SC formulation I having the compositions depicted in Table 5 was prepared.

TABLE 5

| Composition of SC formulation I | | |
|---|---|---|
| Component | Name | Amount %-w/w |
| Active ingredient | Crystalline form A | 15 |
| Dispersant 1 | EO-PO blockcopolymer | 3 |
| Wetting agent | Naphtalene sulfonic acid formaldehyde condensate, Na salt | 4 |
| Thickener | Xanthan gum | 2 |
| Anti-freezing agent | Propylene glycol | 2 |
| Anti-foaming agent | Typical silicon based defoamer, like Silfoam type from Wacker | 0.5 |
| Preservative | Substituted isothiazolin-3-one | 0.2 |
| Solvent | Water | 73.8 |

The remaining water amount is placed into a suitable container. The active ingredient, wetting agent, dispersing agent, preservative, anti-freezing agent is admixed to water. To that preparation is added the active ingredient and part of the anti foaming agent. The mixture is then ground in a bead mill (like a Dyno-Mill type from Bachofen, Switzerland) with sufficent ball loading to ensure effective milling efficiency. A cooling device is attached to the bead mill to ensure proper cooling of the device during the milling procedure. The milling is stopped when the desired particle size distribution as been obtained (measured with Malvern Mastersizer 2000). To the composition is added the remaining amount of anti-foaming agent as well as the thickener under stirring to ensure homogeneous distribution of the component.

Example 15

SC Formulation Containing Crystalline Form B of 3-(difluoromethyl)-1-methyl-N-(3',4',5'-trifluoro[1,1'-biphenyl]-2-yl)-1H-pyrazole-4-carboxamide A similar SC formulation was prepared as described under Example 14 but using form B (formulation II).

TABLE 6

Composition of SC-formulation II

| Component | Name | Amount %-w/w |
|---|---|---|
| Active ingredient | Crystalline form B | 15 |
| Dispersant 1 | EO-PO Blockcopolymer | 3 |
| Wetting agent | Naphtalinsulfonic acid form-aldehyde condensate | 4 |
| Thickener | Xanthan gum | 2 |
| Anti-freezing agent | Propylene glycol | 2 |
| Anti-foaming agent | Typical silicon based defoamer, like Silfoam type from Wacker | 0.5 |
| Preservative | Substituted isothiazolin-3-one | 0.2 |
| Solvent | Water | 73.8 |

Assessment of the Formulations:

The obtained formulations were assessed for their stability upon storage at 40° C. for one week. Microscopic pictures of the formulation were taken before and after storage at 40° C. to exemplify the change in particle size. Dispersion stability was assessed using a 2% dilution of the formulation in water in a conical cylinder. The sedimentation volume is recorded after 2 hours of standing. The sediment was collected and analysed using DSC and powder diffraction diffractometry to characterized the solid sediment (giving thus evidence of the sediment amount and crystalline modification present in the sedimentation). The results in table 7 as well as in FIG. 15 clearly demonstrate that the formulation of Example 14 with form A was instable and had significantly more sedimentation and growth in the crystallite size compared to the formulation of Example 15 with form B.

Further it could be shown by DSC and PXRD measurements that the formulated form A underwent phase transformation had converted fully into needle like crystals of form B. The conversion from form A to form B led to complete crystallisation of the active ingredient into the formulation. This would in practice be very unfavourable and cause blocking of nozzle during the application and inhomogeneous distribution of the active ingredient into the formulation.

The formulation of Example 15 with form B as starting material was on the contrary stable in terms of sedimentation, particle size as well as crystalline modification.

TABLE 7

| Formulation analytics | Formulation Example 14 | Formulation Example 15 |
|---|---|---|
| Dispersion stability after storage | | |
| Dispersion stability (2%, 2 h standing) | Traces of sediment | Traces of sediment |

TABLE 7-continued

| Formulation analytics | Formulation Example 14 | Formulation Example 15 |
|---|---|---|
| Particle size distribution (Malvern) | | |
| <2 μm[1] | 61.3% | 54.06% |
| 100%<[2] | 96.8 μm | 65.23 μm |
| Dispersion stability after storage | | |
| Dispersion stability (2%, 2 h standing) | 0.4 ml sediment | Traces of sediment |
| Particle size distribution (Malvern) | | |
| <2 μm[1] | 30.86% | 52.21% |
| 100%<[2] | 440.1 μm | 67.45 μm |

[1]% w/w particle under 2 μm
[2]maximum particle size

Fungicidal Compositions and Use of Crystalline Form B

Just like the amorphous 3-(difluoromethyl)-1-methyl-N-(3',4',5'-trifluoro[1,1'-biphenyl]-2-yl)-1H-pyrazole-4-carboxamide and its crystalline form A, form B is suitable as a fungicide. However, it is superior to this as regards its handling and especially formulation properties. The invention thus also relates to plant protection agents containing the crystalline form B together with formulation auxiliaries usual for the formulation of plant protection agents, in particular plant protection agents in the form of aqueous suspension concentrates (so-called SC's) or non-aqueous suspension concentrates (so-called OD's), and plant protection agents in the form of powders (so-called WP's) and granules (so-called WG's) dispersible in water.

The invention also relates to a process for combating undesired plant growth, which is characterized in that crystalline form B, preferably as a suitable active substance preparation, is used on plants, their habitat and/or on seeds.

Form B of 3-(difluoromethyl)-1-methyl-N-(3',4',5'-trifluoro[1,1'-biphenyl]-2-yl)-1H-pyrazole-4-carboxamide exhibits excellent activity against a broad spectrum of phytopathogenic fungi, in particular from the class of the *Ascomycetes, Deuteromycetes, Basidiomycetes* and *Peronosporomycetes* (syn. *Oomycetes*) and Fungi imperfect Some of them are systemically active and can be used in crop protection as foliar fungicides, as fungicides for seed dressing and as soil fungicides.

Form B is particularly important for the control of a large number of fungi on various crop plants, such as wheat, rye, barley, triticale, oats, rice, corn, grass, bananas, cotton, soybeans, coffee, sugarcane, grapevines, fruit and ornamental plants and vegetables, such as cucumbers, beans, tomatoes, potatoes and cucurbits, and also on the seeds of these plants. They can also be used in crops which are tolerant against attack by insects or fungi or herbicide applications due to breeding, including genetic engineering methods. Moreover, they are suitable for controlling *Botryosphaeria* species, *Cylindrocarpon* species, *Eutypa lata, Neonectria liriodendri* and *Stereum hirsutum*, which attack, inter alia, wood or the roots of grapevines.

Form B of 3-(difluoromethyl)-1-methyl-N-(3',4',5'-trifluoro[1,1'-biphenyl]-2-yl)-1H-pyrazole-4-carboxamide is suitable for controlling *Alternaria* species on vegetables, rapeseed, sugarbeet, fruit, rice, soybeans and on potatoes (for example, *A. solani* or *A. alternate*) and tomatoes (for example, *A. solani* or *A. alternate*) and *Alternaria* ssp. (ear black) on wheat.

Form B of 3-(difluoromethyl)-1-methyl-N-(3',4',5'-trifluoro[1,1'-biphenyl]-2-yl)-1H-pyrazole-4-carboxamide is suitable for controlling *Aphanomyces* species on sugarbeet and vegetables.

Form B of 3-(difluoromethyl)-1-methyl-N-(3',4',5'-trifluoro[1,1'-biphenyl]-2-yl)-1H-pyrazole-4-carboxamide is suitable for controlling *Ascochyta* species on cereals and vegetables, for example *Ascochyta tritici* (leaf spot) on wheat.

Form B of 3-(difluoromethyl)-1-methyl-N-(3',4',5'-trifluoro[1,1'-biphenyl]-2-yl)-1H-pyrazole-4-carboxamide is suitable for controlling *Bipolaris* and *Drechslera* species on corn (for example *D. Maydis*), cereals, rice and lawns.

Form B of 3-(difluoromethyl)-1-methyl-N-(3',4',5'-trifluoro[1,1'-biphenyl]-2-yl)-1H-pyrazole-4-carboxamide is suitable for controlling *Blumeria graminis* (powdery mildew) on cereals (for example, wheat or barley).

Form B of 3-(difluoromethyl)-1-methyl-N-(3',4',5'-trifluoro[1,1'-biphenyl]-2-yl)-1H-pyrazole-4-carboxamide is suitable for controlling Botrytis cinerea (gray mold) on strawberries, vegetables, flowers, grapevines and wheat (ear mildew).

Form B of 3-(difluoromethyl)-1-methyl-N-(3',4',5'-trifluoro[1,1'-biphenyl]-2-yl)-1H-pyrazole-4-carboxamide is suitable for controlling *Bremia lactucae* on lettuce.

Form B of 3-(difluoromethyl)-1-methyl-N-(3',4',5'-trifluoro[1,1'-biphenyl]-2-yl)-1H-pyrazole-4-carboxamide is suitable for controlling *Cercospora* species on corn, rice, sugarbeet and, for example, *Cercospora sojina* (leaf spot) or *Cercospora kikuchii* (leaf spot) on soybeans.

Form B of 3-(difluoromethyl)-1-methyl-N-(3',4',5'-trifluoro[1,1'-biphenyl]-2-yl)-1H-pyrazole-4-carboxamide is suitable for controlling *Cladosporium herbarum* (ear black) in wheat.

Form B of 3-(difluoromethyl)-1-methyl-N-(3',4',5'-trifluoro[1,1'-biphenyl]-2-yl)-1H-pyrazole-4-carboxamide is suitable for controlling *Cochliobolus* species on corn, cereals (for example, *Cochliobolus sativus*) and rice (for example *Cochliobolus miyabeanus*).

Form B of 3-(difluoromethyl)-1-methyl-N-(3',4',5'-trifluoro[1,1'-biphenyl]-2-yl)-1H-pyrazole-4-carboxamide is suitable for controlling *Colletotricum* species on cotton and, for example, *Colletotrichum truncatum* (*Antracnose*) on soybeans.

Form B of 3-(difluoromethyl)-1-methyl-N-(3',4',5'-trifluoro[1,1'-biphenyl]-2-yl)-1H-pyrazole-4-carboxamide is suitable for controlling *corynespora cassiicola* (leaf spot) on soybeans.

Form B of 3-(difluoromethyl)-1-methyl-N-(3',4',5'-trifluoro[1,1'-biphenyl]-2-yl)-1H-pyrazole-4-carboxamide is suitable for controlling *Dematophora necatrix* (root/stem rot) on soybeans.

Form B of 3-(difluoromethyl)-1-methyl-N-(3',4',5'-trifluoro[1,1'-biphenyl]-2-yl)-1H-pyrazole-4-carboxamide is suitable for controlling *Diaporthe phaseolorum* (stem disease) on soybeans.

Form B of 3-(difluoromethyl)-1-methyl-N-(3',4',5'-trifluoro[1,1'-biphenyl]-2-yl)-1H-pyrazole-4-carboxamide is suitable for controlling *Drechslera species, Pyrenophora* species on corn, cereals, rice and lawns, on barley (for example, *D. teres*) and on wheat (for example, *D. tritici-repentis*).

Form B of 3-(difluoromethyl)-1-methyl-N-(3',4',5'-trifluoro[1,1'-biphenyl]-2-yl)-1H-pyrazole-4-carboxamide is suitable for controlling *Esca* on grapevines, caused by *Phaeoacremonium chlamydosporium, Ph. Aleophilum*, and *Formitipora punctata* (syn. *Phellinus punctatus*).

Form B of 3-(difluoromethyl)-1-methyl-N-(3',4',5'-trifluoro[1,1'-biphenyl]-2-yl)-1H-pyrazole-4-carboxamide is suitable for controlling *Elsinoe ampelina* on grapevines.

Form B of 3-(difluoromethyl)-1-methyl-N-(3',4',5'-trifluoro[1,1'-biphenyl]-2-yl)-1H-pyrazole-4-carboxamide is suitable for controlling *Epicoccum* spp. (ear black) on wheat.

Form B of 3-(difluoromethyl)-1-methyl-N-(3',4',5'-trifluoro[1,1'-biphenyl]-2-yl)-1H-pyrazole-4-carboxamide is suitable for controlling *Exserohilum* species on corn.

Form B of 3-(difluoromethyl)-1-methyl-N-(3',4',5'-trifluoro[1,1'-biphenyl]-2-yl)-1H-pyrazole-4-carboxamide is suitable for controlling *Erysiphe cichoracearum* and *Sphaerotheca fuliginea* on cucumbers.

Form B of 3-(difluoromethyl)-1-methyl-N-(3',4',5'-trifluoro[1,1'-biphenyl]-2-yl)-1H-pyrazole-4-carboxamide is suitable for controlling *Fusarium* and *Verticillium* species on various plants: for example, *F. graminearum* or *F. culmorum* (root rot) on cereals (for example, wheat or barley) or, for example, *F. oxysporum* tomatoes and *Fusarium solani* (stem disease) on soybeans.

Form B of 3-(difluoromethyl)-1-methyl-N-(3',4',5'-trifluoro[1,1'-biphenyl]-2-yl)-1H-pyrazole-4-carboxamide is suitable for controlling *Gaeumanomyces graminis* (root black) on cereals (for example, wheat or barley).

Form B of 3-(difluoromethyl)-1-methyl-N-(3',4',5'-trifluoro[1,1'-biphenyl]-2-yl)-1H-pyrazole-4-carboxamide is suitable for controlling *Gibberella* species on cereals and rice (for example *Gibberella fujikuroi*).

Form B of 3-(difluoromethyl)-1-methyl-N-(3',4',5'-trifluoro[1,1'-biphenyl]-2-yl)-1H-pyrazole-4-carboxamide is suitable for controlling *Glomerella cingulata* on grapevines and other plants.

Form B of 3-(difluoromethyl)-1-methyl-N-(3',4',5'-trifluoro[1,1'-biphenyl]-2-yl)-1H-pyrazole-4-carboxamide is suitable for controlling *Grainstaining* complex on rice.

Form B of 3-(difluoromethyl)-1-methyl-N-(3',4',5'-trifluoro[1,1'-biphenyl]-2-yl)-1H-pyrazole-4-carboxamide is suitable for controlling *Guignardia budwelli* on grapevines.

Form B of 3-(difluoromethyl)-1-methyl-N-(3',4',5'-trifluoro[1,1'-biphenyl]-2-yl)-1H-pyrazole-4-carboxamide is suitable for controlling *Helminthosporium* species on corn and rice.

Form B of 3-(difluoromethyl)-1-methyl-N-(3',4',5'-trifluoro[1,1'-biphenyl]-2-yl)-1H-pyrazole-4-carboxamide is suitable for controlling *Isariopsis clavispora* on grapevines.

Form B of 3-(difluoromethyl)-1-methyl-N-(3',4',5'-trifluoro[1,1'-biphenyl]-2-yl)-1H-pyrazole-4-carboxamide is suitable for controlling *Macrophomina phaseolina* (root/stem rot) on soybeans.

Form B of 3-(difluoromethyl)-1-methyl-N-(3',4',5'-trifluoro[1,1'-biphenyl]-2-yl)-1H-pyrazole-4-carboxamide is suitable for controlling *Michrodochium nivale* (snow mold) on cereals (for example, wheat or barley).

Form B of 3-(difluoromethyl)-1-methyl-N-(3',4',5'-trifluoro[1,1'-biphenyl]-2-yl)-1H-pyrazole-4-carboxamide is suitable for controlling *Microsphaera diffusa* (powdery mildew) on soybeans.

Form B of 3-(difluoromethyl)-1-methyl-N-(3',4',5'-trifluoro[1,1'-biphenyl]-2-yl)-1H-pyrazole-4-carboxamide is suitable for controlling *Mycosphaerella* species on cereals, bananas and peanuts, such as, for example, *M. graminicola* on wheat or *M. fijiensis* on bananas.

Form B of 3-(difluoromethyl)-1-methyl-N-(3',4',5'-trifluoro[1,1'-biphenyl]-2-yl)-1H-pyrazole-4-carboxamide is suitable for controlling *Peronospora* species on cabbage (for example, *P. brassicae*), bulbous plants (for example, *P. destructor*) and, for example, *Peronospora manshurica* (downy mildew) on soybeans.

Form B of 3-(difluoromethyl)-1-methyl-N-(3',4',5'-trifluoro[1,1'-biphenyl]-2-yl)-1H-pyrazole-4-carboxamide is suitable for controlling *Phakopsara pachyrhizi* (soya rust) and *Phakopsara meibomiae* (soya rust) on soybeans.

Form B of 3-(difluoromethyl)-1-methyl-N-(3',4',5'-trifluoro[1,1'-biphenyl]-2-yl)-1H-pyrazole-4-carboxamide is suitable for controlling *Phialophora gregata* (stem disease) on soybeans.

Form B of 3-(difluoromethyl)-1-methyl-N-(3',4',5'-trifluoro[1,1'-biphenyl]-2-yl)-1H-pyrazole-4-carboxamide is suitable for controlling *Phomopsis* species on sunflowers, grapevines (for example, *P. viticola*) and soybeans (for example, *Phomopsis phaseoli*).

Form B of 3-(difluoromethyl)-1-methyl-N-(3',4',5'-trifluoro[1,1'-biphenyl]-2-yl)-1H-pyrazole-4-carboxamide is suitable for controlling *Phytophthora* species on various plants, for example, *P. capsici* on bell peppers, *Phytophthora megasperma* (leaf/stem rot) on soybeans, *Phytophthora infestans* on potatoes and tomatoes.

Form B of 3-(difluoromethyl)-1-methyl-N-(3',4',5'-trifluoro[1,1'-biphenyl]-2-yl)-1H-pyrazole-4-carboxamide is suitable for controlling *Plasmopara viticola* on grapevines.

Form B of 3-(difluoromethyl)-1-methyl-N-(3',4',5'-trifluoro[1,1'-biphenyl]-2-yl)-1H-pyrazole-4-carboxamide is suitable for controlling *Podosphaera leucotricha* on apples.

Form B of 3-(difluoromethyl)-1-methyl-N-(3',4',5'-trifluoro[1,1'-biphenyl]-2-yl)-1H-pyrazole-4-carboxamide is suitable for controlling *Pseudocercosporella herpotrichoides* (eyespot) on cereals (wheat or barley).

Form B of 3-(difluoromethyl)-1-methyl-N-(3',4',5'-trifluoro[1,1'-biphenyl]-2-yl)-1H-pyrazole-4-carboxamide is suitable for controlling *Pseudoperonospora* on various plants, for example, *P. cubensis* on cucumbers or *P. humili* on hops.

Form B of 3-(difluoromethyl)-1-methyl-N-(3',4',5'-trifluoro[1,1'-biphenyl]-2-yl)-1H-pyrazole-4-carboxamide is suitable for controlling *Pseudopezicula tracheiphilai* on grapevines.

Form B of 3-(difluoromethyl)-1-methyl-N-(3',4',5'-trifluoro[1,1'-biphenyl]-2-yl)-1H-pyrazole-4-carboxamide is suitable for controlling *Puccinia* species on various plants, for example, *P. triticina, P. striformins, P. hordei* or *P. graminis* on cereals (for example, wheat or barley), or on asparagus (for example, *P. asparagi*).

Form B of 3-(difluoromethyl)-1-methyl-N-(3',4',5'-trifluoro[1,1'-biphenyl]-2-yl)-1H-pyrazole-4-carboxamide is suitable for controlling *Pyricularia oryzae, Corticium sasakii, Sarocladium oryzae, S. attenuatum, Pyrenophora tritici-repentis* (leaf spot) on wheat or *Pyrenophora teres* (net blotch) on barley.

Form B of 3-(difluoromethyl)-1-methyl-N-(3',4',5'-trifluoro[1,1'-biphenyl]-2-yl)-1H-pyrazole-4-carboxamide is for controlling *Entyloma oryzae* on rice.

Form B of 3-(difluoromethyl)-1-methyl-N-(3',4',5'-trifluoro[1,1'-biphenyl]-2-yl)-1H-pyrazole-4-carboxamide is suitable for controlling *Pyricularia grisea* on lawns and cereals.

Form B of 3-(difluoromethyl)-1-methyl-N-(3',4',5'-trifluoro[1,1'-biphenyl]-2-yl)-1H-pyrazole-4-carboxamide is suitable for controlling *Pythium* spp. on lawns, rice, corn, wheat, cotton, rapeseed, sunflowers, sugarbeet, vegetables and other plants (for example, *P. ultiumum* or *P. aphanidermatum*).

Form B of 3-(difluoromethyl)-1-methyl-N-(3',4',5'-trifluoro[1,1'-biphenyl]-2-yl)-1H-pyrazole-4-carboxamide is suitable for controlling *Ramularia collo-cygni* (*Ramularia*/sunburn complex/physiological leaf spots) on barley.

Form B of 3-(difluoromethyl)-1-methyl-N-(3',4',5'-trifluoro[1,1'-biphenyl]-2-yl)-1H-pyrazole-4-carboxamide is suitable for controlling *Rhizoctonia* species on cotton, rice, potatoes, lawns, corn, rapeseed, potatoes, sugarbeet, vegetables and on various plants for example, *Rhizoctonia solani* (root/stem rot) on soybeans or *Rhizoctonia cerealis* (sharp eyspot) on wheat or barley.

Form B of 3-(difluoromethyl)-1-methyl-N-(3',4',5'-trifluoro[1,1'-biphenyl]-2-yl)-1H-pyrazole-4-carboxamide is suitable for controlling *Rhynchosporium secalis* on barley (leaf spot), rye and triticale.

Form B of 3-(difluoromethyl)-1-methyl-N-(3',4',5'-trifluoro[1,1'-biphenyl]-2-yl)-1H-pyrazole-4-carboxamide is suitable for controlling *Sclerotinia* species on rapeseed and sunflowers, and, for example, *Sclerotinia sclerotiorum* (stem disease) or *Sclerotinia rolfsii* (stem disease) on soybeans.

Form B of 3-(difluoromethyl)-1-methyl-N-(3',4',5'-trifluoro[1,1'-biphenyl]-2-yl)-1H-pyrazole-4-carboxamide is suitable for controlling *Septoria glycines* (leaf spot) on soybeans.

Form B of 3-(difluoromethyl)-1-methyl-N-(3',4',5'-trifluoro[1,1'-biphenyl]-2-yl)-1H-pyrazole-4-carboxamide is suitable for controlling *Septoria tritici* (leaf septoria) and *Stagonospora nodorum* on wheat.

Form B of 3-(difluoromethyl)-1-methyl-N-(3',4',5'-trifluoro[1,1'-biphenyl]-2-yl)-1H-pyrazole-4-carboxamide is suitable for controlling *Erysiphe* (syn. *Uncinula*) necator on grapevines.

Form B of 3-(difluoromethyl)-1-methyl-N-(3',4',5'-trifluoro[1,1'-biphenyl]-2-yl)-1H-pyrazole-4-carboxamide is suitable for controlling *Setospaeria* species on corn and lawns.

Form B of 3-(difluoromethyl)-1-methyl-N-(3',4',5'-trifluoro[1,1'-biphenyl]-2-yl)-1H-pyrazole-4-carboxamide is suitable for controlling *Sphacelotheca reilinia* on corn.

Form B of 3-(difluoromethyl)-1-methyl-N-(3',4',5'-trifluoro[1,1'-biphenyl]-2-yl)-1H-pyrazole-4-carboxamide is suitable for controlling *Stagonospora nodorum* (ear septoria) on wheat.

Form B of 3-(difluoromethyl)-1-methyl-N-(3',4',5'-trifluoro[1,1'-biphenyl]-2-yl)-1H-pyrazole-4-carboxamide is suitable for controlling *Thievaliopsis* species on soybeans and cotton.

Form B of 3-(difluoromethyl)-1-methyl-N-(3',4',5'-trifluoro[1,1'-biphenyl]-2-yl)-1H-pyrazole-4-carboxamide is suitable for controlling *Tilletia species* on cereals.

Form B of 3-(difluoromethyl)-1-methyl-N-(3',4',5'-trifluoro[1,1'-biphenyl]-2-yl)-1H-pyrazole-4-carboxamide is suitable for controlling *Typhula incarnata* (snow rot) on wheat or barley.

Form B of 3-(difluoromethyl)-1-methyl-N-(3',4',5'-trifluoro[1,1'-biphenyl]-2-yl)-1H-pyrazole-4-carboxamide is suitable for controlling *Ustilago* species on cereals, corn (for example, *U. maydis*) and sugarcane.

Form B of 3-(difluoromethyl)-1-methyl-N-(3',4',5'-trifluoro[1,1'-biphenyl]-2-yl)-1H-pyrazole-4-carboxamide is suitable for controlling *Venturia* species (scab) on apples (for example, *V. inaequalis*) and pears.

Form B of 3-(difluoromethyl)-1-methyl-N-(3',4',5'-trifluoro[1,1'-biphenyl]-2-yl)-1H-pyrazole-4-carboxamide is also suitable for controlling harmful fungi in the protection of materials (for example wood, paper, paint dispersions, fibers or fabrics) and in the protection of stored products. In the protection of wood, particular attention is paid to the following harmful fungi: *Ascomycetes*, such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; *Basidiomycetes*, such as *Coniophora* spp., *Coriolus* spp., *Gloeophyllum* spp., *Lentinus* spp., *Pleurotus* spp., *Poria* spp., *Serpula* spp. and *Tyromyces* spp., *Deuteromycetes*, such as *Aspergillus* spp., *Cladosporium* spp., *Penicillium* spp., *Trichoderma* spp., *Alternaria* spp., *Paecilomyces* spp. and *Zygomycetes*, such as *Mucor* spp., additionally in the protection of materials the following yeasts: *Candida* spp. and *Saccharomyces cerevisae*.

Form B of 3-(difluoromethyl)-1-methyl-N-(3',4',5'-trifluoro[1,1'-biphenyl]-2-yl)-1H-pyrazole-4-carboxamide is employed by treating the fungi or the plants, seeds or materials to be protected against fungal attack or the soil with a fungicidally effective amount of the active compound. Application can be both before and after the infection of the materials, plants or seeds by the fungi.

Accordingly, the invention furthermore provides a method for controlling phytopathogenic fungi wherein the fungi or the materials, plants, the soil or seed to be protected against fungal attack are/is treated with an effective amount of form B of 3-(difluoroämethyl)-1-methyl-N-(3',4',5'-trifluoro[1,1'-biphenyl]-2-yl)-1H-pyrazole-4-carboxamide.

The invention furthermore provides a composition for controlling phytopathogenic fungi, which composition comprises form B of 3-(difluoromethyl)-1-methyl-N-(3',4',5'-trifluoro[1,1'-biphenyl]-2-yl)-1H-pyrazole-4-carboxamide and at least one solid or liquid carrier.

The fungicidal compositions generally comprise between 0.1 and 95% by weight, preferably between 0.5 and 90% by weight, of active compound.

When employed in crop protection, the application rates are, depending on the kind of effect desired, between 0.01 and 2.0 kg of active compound per ha.

In seed treatment, the amounts of active compound required are generally from 1 to 1000 g/100 kg of seed, preferably from 5 to 100 g/100 kg of seed.

When used in the protection of materials or stored products, the active compound application rates depend on the kind of application area and on the desired effect. Amounts typically applied in the protection of materials are, for example, from 0.001 g to 2 kg, preferably from 0.005 g to 1 kg, of active compound per cubic meter of treated material.

Form B of 3-(difluoromethyl)-1-methyl-N-(3',4',5'-trifluoro[1,1'-biphenyl]-2-yl)-1H-pyrazole-4-carboxamide can be converted into customary formulations, for example solutions, emulsions, suspensions, dusts, powders, pastes and granules. The application form depends on the particular purpose; in each case, it should ensure a fine and uniform distribution of the compound according to the invention.

The formulations are prepared in a known manner, for example by extending the active compound with solvents and/or carriers, if desired using emulsifiers and dispersants. Solvents/auxiliaries suitable for this purpose are essentially:

water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone, N-octylpyrrolidone), acetates (glycol diacetate), glycols, fatty acid dimethylamides, fatty acids and fatty acid esters. In principle, solvent mixtures may also be used.

carriers such as ground natural minerals (for example kaolins, clays, talc, chalk) and ground synthetic minerals (for example finely divided silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable for use as surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound. The active compounds are employed in a purity of from 90% to 100%, preferably 95% to 100% (according to NMR spectrum).

A preferred embodiment of the invention relates to liquid formulations of form B. In addition to the solid active substance phase, these have at least one liquid phase, in which 3-(difluoromethyl)-1-methyl-N-(3',4',5'-trifluoro[1,1'-biphenyl]-2-yl)-1H-pyrazole-4-carboxamide is present in form B in the form of dispersed fine particles. Possible liquid phases are essentially water and those organic solvents in which form B is only slightly soluble, or insoluble, for example those wherein the solubility of form B at 25° C. and 1013 mbar is not more than 1 wt. %, in particular not more than 0.1 wt. %, and especially not more than 0.01 wt. %.

According to a first preferred embodiment, the liquid phase consists of water and aqueous solvents, i.e. solvent mixtures which in addition to water also contain up to 20 wt. %, preferably however not more than 10 wt. %, based on the total quantity of water and solvent, of one or more organic solvents miscible with water, for example ethers miscible with water such as tetrahydro-furan, methyl glycol, methyl diglycol, alkanols such as isopropanol or polyols such as glycol, glycerine, diethylene glycol, propylene glycol and the like. Such formulations are also referred to below as suspension concentrates (SCs).

Such suspension concentrates contain 3-(difluoromethyl)-1-methyl-N-(3',4',5'-trifluoro[1,1-biphenyl]-2-yl)-1H-pyrazole-4-carboxamide as form B in a finely divided particulate form, wherein the particles of form B are present suspended in an aqueous phase. The size of the active substance particles, i.e. the size which 90 wt. % of the active substance particles do not exceed, here typically lies below 30 μm, in particular below 20 μm. Advantageously, in the SCs according to the invention, at least 40 wt. % and in particular at least 60 wt. % of the particles have diameters below 2 μm.

In such SCs the quantity of active substance, i.e. the total quantity of carboxamide and of other active substances if necessary, usually lies in the range from 10 to 70 wt. %, in particular in the range from 20 to 50 wt. %, based on the total weight of the suspension concentrate.

In addition to the active substance, aqueous suspension concentrates typically contain surface-active substances, and also if necessary antifoaming agents, thickeners (=rheology modifiers), antifreeze agents, stabilizers (biocides), agents for adjusting the pH and anticaking agents.

Possible surface-active substances are the previously named surface-active substances. Preferably the aqueous plant protection agents according to the invention contain at least one of the previously named anionic surfactants and if necessary one or more nonionic surfactants, if necessary in combination with a protective colloid. The quantity of surface-active substances will as a rule be 1 to 50 wt. %, in particular 2 to 30 wt. %, based on the total weight of the aqueous SCs according to the invention. Preferably the surface-active substances include at least one anionic surface-active substance and at least one nonionic surface-active substance, and the proportion of anionic to nonionic surface-active substance typically lies in the range from 10:1 to 1:10.

Concerning the nature and quantity of the antifoaming agents, thickeners, antifreeze agents and biocides, the same applies as aforesaid.

If necessary, the aqueous SCs according to the invention can contain buffers for pH regulation. Examples of buffers are alkali metal salts of weak inorganic or organic acids, such as for example phosphoric acid, boric acid, acetic acid, propionic acid, citric acid, fumaric acid, tartaric acid, oxalic acid and succinic acid.

According to a first preferred embodiment, the liquid phase consists of non-aqueous organic solvents in which the solubility of form B of 3-(difluoromethyl)-1-methyl-N-(3',4',5'-trifluoro[1,1-biphenyl]-2-yl)-1H-pyrazole-4-carboxamide at 25° C. and 1013 mbar is not more than 1 wt. %, in particular not more than 0.1 wt. %, and especially not more than 0.01 wt. %. These include in particular aliphatic and cycloaliphatic hydrocarbons and oils, in particular those of plant origin, and also $C_1$-$C_4$ alkyl esters of saturated or unsaturated fatty acids or fatty acid mixtures, in particular the methyl esters, for example methyl oleate, methyl stearate and rape oil methyl ester, but also paraffinic mineral oils and the like. Accordingly, the present invention relates also to agents for plant protection in the form of a non-aqueous suspension concentrate, which will also be referred to below as OD (oil-dispersion). Such ODs contain form B of 3-(difluoromethyl)-1-methyl-N-(3',4',5'-trifluoro[1,1'-biphenyl]-2-yl)-1H-pyrazole-4-carboxamide in a finely divided particulate form, wherein the particles of form B are present suspended in a non-aqueous phase. The size of the active substance particles, i.e. the size which 90 wt. % of the active substance particles do not exceed, here typically lies below 30 μm, in particular below 20 μm. Advantageously, in the non-aqueous suspension concentrates, at least 40 wt. % and in particular at least 60 wt. % of the particles have diameters below 2 μm.

In such ODs, the quantity of active substance, i.e. the total quantity of carboxamide and of other active substances if necessary, usually lies in the range from 10 to 70 wt. %, in particular in the range from 20 to 50 wt. %, based on the total weight of the non-aqueous suspension concentrate.

In addition to the active substance and the liquid carrier, non-aqueous suspension concentrates typically contain surface-active substances, and also if necessary antifoaming agents, agents to modify the rheology and stabilizers (biocides).

Possible surface-active substances are preferably the previously named anionic and nonionic surfactants. The quantity of surface-active substances will as a rule be 1 to 30 wt. %, in particular 2 to 20 wt. %, based on the total weight of the non-aqueous SCs according to the invention. Preferably the surface-active substances include at least one anionic surface-active substance and at least one nonionic surface-active substance, and the proportion of anionic to nonionic surface-active substance typically lies in the range from 10:1 to 1:10.

Form B of 3-(difluoromethyl)-1-methyl-N-(3',4',5'-trifluoro[1,1'-biphenyl]-2-yl)-1H-pyrazole-4-carboxamide according to the invention can also be formulated as solid plant protection agents. These include powder, scattering and dusting agents but also water-dispersible powders and granules, for example coated, impregnated and homogenous granules. Such formulations can be produced by mixing or simultaneous grinding of form B of 3-(difluoromethyl)-1-methyl-N-(3',4',5'-trifluoro[1,1'-biphenyl]-2-yl)-1H-pyrazole-4-carboxamide with a solid carrier and if necessary other additives, in particular surface-active substances. Granules can be produced by binding of the active substances to solid carriers. Solid carriers are mineral earths such as silicic acids, silica gels, silicates, talc, kaolin, limestone, lime, chalk, bole, loess, clay, dolomite, diatomaceous earth, calcium and magnesium sulfate, magnesium oxide, ground plastics, fertilizers such as ammonium sulfate, ammonium phosphate, ammonium nitrate, ureas and plant products such as cereal flour, tree bark, wood and nutshell flour, cellulose powder or other solid carriers. Solid formulations can also be produced by spray drying, if necessary in the presence of polymeric or inorganic drying aids, and if necessary in the presence of solid carriers. For the production of solid formulations of 3-(difluoromethyl)-1-methyl-N-(3',4',5'-trifluoro[1,1'-biphenyl]-2-yl)-1H-pyrazole-4-carboxamide of form B, extrusion processes, fluidized bed granulation, spray granulation and comparable technologies are suitable.

Possible surface-active substances are the previously named surfactants and protective colloids. The quantity of surface-active substances will as a rule be 1 to 30 wt. %, in particular 2 to 20 wt. %, based on the total weight of the solid formulation according to the invention.

In such solid formulations, the quantity of active substance, i.e. the total quantity of carboxamide and of other active substances if necessary, usually lies in the range from 10 to 70 wt. %, in particular in the range from 20 to 50 wt. %, based on the total weight of the non-aqueous suspension concentrate.

The following formulation examples illustrate the production of such preparations:

I. Water-dispersible powder:
20 parts by weight of form B are mixed well with 3 parts by weight of the sodium salt of diisobutylnaphthalenesulfonic acid, 17 parts by weight of the sodium salt of a ligninsulfonic acid from a sulfite waste liquor and 60 parts by weight of powdered silica gel and ground in a hammer mill. In this manner, a water-dispersible powder which contains form B is obtained.

II. Dusting agent 5 parts by weight of form B are mixed with 95 parts by weight of finely divided kaolin. In this manner, a dusting agent which contains 5 wt. % of form B is obtained.

III. Non-aqueous suspension concentrate:

20 parts by weight of form B are mixed intimately with 2 parts by weight of the calcium salt of dodecylbenzenesulfonic acid, 8 parts by weight of fatty alcohol polyglycol ether, 2 parts by weight of the sodium salt of a phenolsulfonic acid urea formaldehyde condensate and 68 parts by weight of a paraffinic mineral oil. A stable, non-aqueous suspension concentrate of form B is obtained.

IV. Non-aqueous suspension concentrate:

20 parts by weight of form B are ground to a fine active substance suspension in an agitator ball mill with the addition of 10 parts by weight of dispersants and wetting agents and 70 parts by weight of a paraffinic mineral oil. A stable, non-aqueous suspension concentrate of form B is obtained. On dilution in water, a stable suspension of the active substance is obtained. The active substance content in the formulation is 20 wt. %.

V. Aqueous suspension concentrate:

10 parts by weight of form B are formulated as an aqueous suspension concentrate in a solution of 17 parts by weight of a poly(ethylene glycol) (propylene glycol) block copolymer, 2 parts by weight of a phenolsulfonic acid formaldehyde condensate and about 1 part by weight of other additives (thickeners, foam suppressants) in a mixture of 7 parts by weight of propylene glycol and 63 parts by weight of water.

VI. Aqueous suspension concentrate:

20 parts by weight of form B are ground to a fine active substance suspension in a stirred ball mill with the addition of 10 parts by weight of dispersants and wetting agents and 70 parts by weight of water. On dilution in water, a stable suspension of the active substance is obtained. The active substance content in the formulation is 20 wt. %.

VII. Water-dispersible and water-soluble granules 50 parts by weight of form B are finely ground with the addition of 50 parts by weight of dispersants and wetting agents and formulated as water-dispersible or water-soluble granules by means of industrial devices (for example extrusion, spray tower, fluidized bed). On dilution in water, a stable dispersion or solution of the active substance is obtained. The formulation has an active substance content of 50 wt. %.

VIII. Water-dispersible and water-soluble powder 75 parts by weight of form B are ground in a rotor-stator mill with the addition of 25 parts by weight of dispersants and wetting agents and also silica gel. On dilution in water, a stable dispersion or solution of the active substance is obtained. The active substance content of the formulation is 75 wt. %.

IX. Gel formulations:

20 parts by weight of form B, 10 parts by weight of dispersant, 1 part by weight of gelling agent and 70 parts by weight of water or an organic solvent are ground to a fine suspension in a ball mill. On dilution in water, a stable suspension is obtained. The active substance content of the formulation is 20 wt. %.

X. Directly usable granules (GR, FG, GG, MG)

0.5 parts by weight of form B are finely ground and combined with 99.5 parts by weight of carriers. Common processes here are extrusion, spray drying or fluidized bed. Granules for direct application with 0.5 wt. % active substance content are thus obtained.

Suspensions (FS), dusts (DS), water-dispersible and water-soluble powders (WS, SS) are usually used for the treatment of seed. These formulations can be applied to the seed in undiluted or, preferably, diluted form. The application can be carried out before sowing.

The active compound can be used as such, in the form of its formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; the intention is to ensure in each case the finest possible distribution of the active compound according to the invention.

Aqueous use forms can be prepared from pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compound may also be used successfully in the ultra-low-volume process (ULV), by which it is possible to apply formulations comprising over 95% by weight of active compound, or even to apply the active compound without additives.

Various types of oils, wetters, adjuvants, herbicides, fungicides, other pesticides, or bactericides may be added to the active compound, if appropriate not until immediately prior to use (tank mix). These compositions can be admixed with the compositions according to the invention in a weight ratio of from 1:100 to 100:1, preferably from 1:10 to 10:1.

The following are particularly suitable as adjuvants in this context: organically modified polysiloxanes, for example Break Thru S 240®; alcohol alkoxylates, for example Atplus 245®, Atplus MBA 1303®, Plurafac LF 300® and Lutensol ON 30®; EO-PO block polymers, for example Pluronic RPE 2035® and Genapol B®; alcohol ethoxylates, for example Lutensol XP 80®; and sodium dioctylsulfosuccinate, for example Leophen RA®.

Form B of 3-(difluoromethyl)-1-methyl-N-(3',4',5'-trifluoro[1,1'-biphenyl]-2-yl)-1H-pyrazole-4-carboxamide in the application form as fungicide can also be present together with other active compounds, for example with herbicides, insecticides, growth regulators, fungicides or else with fertilizers. When mixing the compounds or the compositions comprising them with one or more further active compounds, in particular fungicides, it is in many cases possible, for example, to widen the activity spectrum or to prevent the development of resistance. In many cases, synergistic effects are obtained.

The present invention furthermore provides a combination of form B of 3-(difluoromethyl)-1-methyl-N-(3',4',5'-trifluoro[1,1'-biphenyl]-2-yl)-1H-pyrazole-4-carboxamide and at least one further fungicidal, insecticidal, herbicidal and/or growth-regulating active compound.

The following list of fungicides with which the compounds according to the invention can be applied together is meant to illustrate the possible combinations, but not to limit them:

strobilurins azoxystrobin, dimoxystrobin, enestroburin, fluoxastrobin, kresoxim-methyl, metominostrobin, picoxystrobin, pyraclostrobin, trifloxystrobin, orysastrobin, methyl(2-chloro-5-[1-(3-methylbenzyloxyimino)ethyl]benzyl)carbamate, methyl(2-chloro-5-[1-(6-methylpyridin-2-ylmethoxyimino) ethyl]benzyl)carbamate, methyl 2-(ortho-(2,5-dimethylphenyloxymethylene)phenyl)-3-methoxyacrylate;

carboxamides carboxanilides: benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(3',4'-dichloro-5-flurobiphenyl-2-yl)-3-difluoromethyl-1-methylpyrazole-4-carboxamide, N-(2-cyanophenyl)-3,4-dichloroisothiazole-5-carboxamide;

carboxylic acid morpholides: dimethomorph, flumorph;

benzamides: flumetover, fluopicolide (picobenzamid), zoxamide;

other carboxamides: carpropamid, diclocymet, mandipropamid, N-(2-(4-[3-(4-chlorophenyl)prop-2-ynyloxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide;

azoles triazoles: bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole;

imidazoles: cyazofamid, imazalil, pefurazoate, prochloraz, triflumizole;

benzimidazoles: benomyl, carbendazim, fuberidazole, thiabendazole;

others: ethaboxam, etridiazole, hymexazole;

nitrogenous heterocyclyl compounds pyridines: fluazinam, pyrifenox, 3-[5-(4-chlorophenyl)-2,3-dimethylisoxazolidin-3-yl]-pyridine;

pyrimidines: bupirimate, cyprodinil, ferimzone, fenarimol, mepanipyrim, nuarimol, pyrimethanil;

piperazines: triforine;

pyrroles: fludioxonil, fenpiclonil;

morpholines: aldimorph, dodemorph, fenpropimorph, tridemorph;

dicarboximides: iprodione, procymidone, vinclozolin;

others: acibenzolar-S-methyl, anilazine, captan, captafol, dazomet, diclomezine, fenoxanil, folpet, fenpropidin, famoxadone, fenamidone, octhilinone, probenazole, proquinazid, pyroquilon, quinoxyfen, tricyclazole, 5-chloro-7-(4-methylpiperidin-1-yl)-6-(2,4,6-trifluorophenyl)-[1,2,4]triazolo[1,5-a]pyrimidine, 6-(3,4-dichlorophenyl)-5-methyl-[1,2,4]triazolo[1,5-a]pyrimidin-7-ylamine, 6-(4-tert-butylphenyl)-5-methyl-[1,2,4]triazolo[1,5-a]pyrimidin-7-ylamine, 5-methyl-6-(3,5,5-trimethylhexyl)-[1,2,4]triazolo[1,5-a]pyrimidin-7-ylamine, 5-methyl-6-octyl-[1,2,4]triazolo[1,5-a]pyrimidin-7-ylamine, 5-ethyl-6-octyl-[1,2,4]triazolo[1,5-a]pyrimidin-2,7-diamine, 6-ethyl-5-octyl-[1,2,4]triazolo[1,5-a]pyrimidin-7-ylamine, 5-ethyl-6-octyl-[1,2,4]triazolo[1,5-a]pyrimidin-7-ylamine, 5-ethyl-6-(3,5,5-trimethylhexyl)-[1,2,4]triazolo[1,5-a]pyrimidin-7-ylamine, 6-octyl-5-propyl-[1,2,4]triazolo[1,5-a]pyrimidin-7-ylamine, 5-methoxymethyl-6-octyl-[1,2,4]triazolo[1,5-a]pyrimidin-7-ylamine, 6-octyl-5-trifluoromethyl-[1,2,4]triazolo[1,5-a]pyrimidin-7-ylamine, 5-trifluoromethyl-6-(3,5,5-trimethylhexyl)-[1,2,4]triazolo[1,5-a]pyrimidin-7-ylamine, 2-butoxy-6-iodo-3-propylchromen-4-one, N,N-dimethyl-3-(3-bromo-6-fluoro-2-methylindole-1-sulfonyl)-[1,2,4] triazole-1-sulfonamide;

carbamates and dithiocarbamates dithiocarbamates: ferbam, mancozeb, maneb, metiram, metam, propineb, thiram, zineb, ziram;

carbamates: diethofencarb, flubenthiavalicarb, iprovalicarb, propamocarb, methyl 3-(4-chlorophenyl)-3-(2-isopropoxycarbonylamino-3-methylbutyrylamino)propionate, 4-fluorophenyl N-(1-(1-(4-cyanophenyl) ethanesulfonyl)but-2-yl)carbamate;

other fungicides guanidines: dodine, iminoctadine, guazatine;

antibiotics: kasugamycin, polyoxins, streptomycin, validamycin A;

organometallic compounds: fentin salts;

sulfur-containing heterocyclyl compounds: isoprothiolane, dithianon;

organophosphorus compounds: edifenphos, fosetyl, fosetyl-aluminum, iprobenfos, pyrazophos, tolclofos-methyl, phosphorous acid and its salts;

organochlorine compounds: thiophanate-methyl, chlorothalonil, dichlofluanid, tolyifluanid, flusulfamide, phthalide, hexachlorobenzene, pencycuron, quintozene;

nitrophenyl derivatives: binapacryl, dinocap, dinobuton;

inorganic active compounds: Bordeaux mixture, copper acetate, copper hydroxide, copper oxychloride, basic copper sulfate, sulfur;

others: spiroxamine, cyflufenamid, cymoxanil, metrafenone.

The active compounds mentioned above, their preparation and their action against harmful fungi are generally known (cf.: http://www.hclrss.demon.co.uk/index.html); they are commercially available. The compounds named according to IUPAC, their preparation and their fungicidal action are likewise known [cf. EP-A 226 917; EP-A 10 28 125; EP-A 10 35 122; EP-A 12 01 648; WO 98/46608; WO 99/24413; WO 03/14103; WO 03/053145; WO 03/066609; WO 04/049804 and WO 07/012598].

The invention claimed is:

1. A crystalline form B of 3-(difluormethyl)-1-methyl-N-(3',4',5'-trifluor[1,1'-biphenyl]-2-yl)-1H-pyrazol-4-carboxamide, wherein an X-ray powder diffraction diagram at 25° C. and Cu—Kα radiation displays at least 3 of the following reflections, quoted as 2θ values: 6.2±0.2°, 9.2±0.2°, 13.2±0.2°, 14.9±0.2°, 17.7±0.2°, 18.6±0.2°, 23.1±0.2°, 27.6°±0.2°, 30.5±0.2°.

2. A crystalline form B of 3-(difluormethyl)-1-methyl-N-(3',4',5'-trifluor[1,1'-biphenyl]-2-yl)-1H-pyrazol-4-carboxamide, comprising characteristic absorption bands by Fourier Transfrom Infrared Spectroscopy at the wavelengths 3256 $cm^{-1}$ and 1639 $cm^{-1}$.

3. The crystalline form B as claimed in claim 1 with a content of 3-(difluormethyl)-1-methyl-N-(3',4',5'-trifluor[1,1'-biphenyl]-2-yl)-1H-pyrazol-4-carboxamide of at least 94 wt. %.

4. The crystalline form B as claimed in claim 1 with a content of 3-(difluormethyl)-1-methyl-N-(3',4',5'-trifluor[1,1'-biphenyl]-2-yl)-1H-pyrazol-4-carboxamide of at least 90 wt. % of the crystalline form B.

5. A process for the production of the crystalline form B as claimed in claim 1, comprising:
  i) preparing a solution of 3-(difluormethyl)-1-methyl-N-(3',4',5'-trifluor[1,1'-biphenyl]-2-yl)-1H-pyrazol-4-carboxamide in an organic solvent which is selected from the group consisting of methanol, ethanol, 2-propanol, cyclic ethers, acetic acid, aprotic solvents and aromatic solvents, at 50 to 130° C.,
  ii) cooling the solution at a rate between 20° C./hour and 0.1° C./hour to a temperature between 70° C. and (−20)° C., and
  iii) separating form B from the mother liquor.

6. A process for the production of the crystalline form B as claimed in claim 1, comprising
  i) preparing a solution of 3-(difluormethyl)-1-methyl-N-(3',4',5'-trifluor[1,1'-biphenyl]-2-yl)-1H-pyrazol-4-carboxamide in an organic solvent which is selected from the group consisting of methanol, ethanol, 2-propanol, cyclic ethers, acetic acid, aprotic solvents and aromatic solvents, at 50 to 130° C.,
  ii) adding a solubility-decreasing solvent to the solution over a period from 40 minutes to 2.5 hours, and
  iii) separating form B from the mother liquor.

7. A process for the production of the crystalline form B as claimed in claim 1, comprising heating the amorphous compound, its crystalline form A, a mixture of the amorphous form with form A or mixtures of form B with the amorphous form or form A at 80° C. to 154° C.

8. A process for the production of the crystalline form B as claimed in claim 2, comprising:
  i) preparing a solution of 3-(difluormethyl)-1-methyl-N-(3',4',5'-trifluor[1,1'-biphenyl]-2-yl)-1H-pyrazol-4-carboxamide in an organic solvent which is selected from the group consisting of methanol, ethanol, 2-propanol, cyclic ethers, acetic acid, aprotic solvents and aromatic solvents, at 50 to 130° C.,
  ii) cooling the solution at a rate between 20° C./hour and 0.1° C./hour to a temperature between 70° C. and (−20)° C., and
  iii) separating form B from the mother liquor.

9. A process for the production of the crystalline form B as claimed in claim 2, comprising
  i) preparing a solution of 3-(difluormethyl)-1-methyl-N-(3',4',5'-trifluor[1,1'-biphenyl]-2-yl)-1H-pyrazol-4-carboxamide in an organic solvent which is selected from the group consisting of methanol, ethanol, 2-propanol, cyclic ethers, acetic acid, aprotic solvents and aromatic solvents, at 50 to 130° C.,
  ii) adding a solubility-decreasing solvent to the solution over a period from 40 minutes to 2.5 hours, and
  iii) separating form B from the mother liquor.

10. A process for the production of the crystalline form B as claimed in claim 2, comprising heating the amorphous compound, its crystalline form A, a mixture of the amorphous form with form A or mixtures of form B with the amorphous form or form A at 80° C. to 154° C.

11. A plant protection agent containing 3-(difluormethyl)-1-methyl-N-(3',4',5'-trifluor[1,1'-biphenyl]-2-yl)-1H-pyrazol-4-carboxamide which consists of at least 90 wt. % of the crystalline form B as claimed in claim 1, and one or more additives normal for the formulation of plant protection agents.

12. The plant protection agent as claimed in claim 11 in the form of an aqueous suspension concentrate.

13. The plant protection agent as claimed in claim 11 in the form of a non-aqueous suspension concentrate.

14. The plant protection agent as claimed in claim 11 in the form of a powder or granules dispersible in water.

15. A method for combating undesired plant growth, comprising treating the plant, the habitat thereof and/or the seeds with an effective amount of 3-(difluormethyl)-1-methyl-N-(3',4',5'-trifluor[1,1'-biphenyl]-2-yl)-1H-pyrazol-4-carboxamide consisting of at least 90 wt. % of the crystalline form B as claimed in claim 1.

16. A method for combating undesired plant growth, comprising treating the plant, the habitat thereof and/or the seeds with an effective amount of 3-(difluormethyl)-1-methyl-N-(3',4',5'-trifluor[1,1'-biphenyl]-2-yl)-1H-pyrazol-4-carboxamide consisting of at least 90 wt. % of the crystalline form B as claimed in claim 2.

* * * * *